United States Patent
Pfaltz et al.

(10) Patent No.: US 7,435,840 B2
(45) Date of Patent: *Oct. 14, 2008

(54) METHOD FOR PRODUCING ORTHOMETALATED AND ORTHOSUBSTITUTED METALLOCENES

(75) Inventors: Andreas Pfaltz, Binningen (CH); Matthias Lotz, Basel (CH); Marc Schönleber, Rochestown (IE); Benoît Pugin, Münchenstein (CH); Martin Kesselgruber, Basel (CH); Marc Thommen, Nuglar (CH)

(73) Assignee: Solvias AG, Basel (CH)

( * ) Notice: Subject to any disclaimer, the term of this patent is extended or adjusted under 35 U.S.C. 154(b) by 15 days.

This patent is subject to a terminal disclaimer.

(21) Appl. No.: 10/582,404

(22) PCT Filed: Dec. 10, 2004

(86) PCT No.: PCT/EP2004/053388

§ 371 (c)(1),
(2), (4) Date: Jun. 9, 2006

(87) PCT Pub. No.: WO2005/056566

PCT Pub. Date: Jun. 23, 2005

(65) Prior Publication Data

US 2007/0149796 A1 Jun. 28, 2007

(30) Foreign Application Priority Data

Dec. 12, 2003 (CH) .................................. 2134/03

(51) Int. Cl.
*C07F 15/00* (2006.01)
*B01J 31/00* (2006.01)
(52) U.S. Cl. ..................... 556/16; 502/102; 502/104
(58) Field of Classification Search ............. 556/16
See application file for complete search history.

(56) References Cited

U.S. PATENT DOCUMENTS

| | | | | |
|---|---|---|---|---|
| 4,221,744 | A * | 9/1980 | Unruh ................ | 568/454 |
| 5,627,293 | A * | 5/1997 | Pugin ................. | 556/11 |
| 5,760,264 | A * | 6/1998 | Brieden .............. | 556/22 |
| 5,783,715 | A * | 7/1998 | Pugin ................. | 556/11 |
| 5,817,850 | A * | 10/1998 | Pastor et al. ........ | 556/14 |
| 6,169,192 | B1 * | 1/2001 | Pugin et al. ......... | 556/11 |
| 6,177,528 | B1 * | 1/2001 | LaPointe et al. .... | 526/139 |
| 6,191,284 | B1 * | 2/2001 | Knochel et al. ..... | 548/402 |
| 6,362,354 | B1 * | 3/2002 | Bunel et al. ......... | 556/14 |
| 6,534,657 | B2 * | 3/2003 | Zhang ................. | 548/101 |
| 6,590,115 | B2 * | 7/2003 | Boaz et al. .......... | 556/22 |
| 6,620,954 | B1 * | 9/2003 | Boaz .................. | 556/16 |
| 6,777,567 | B2 * | 8/2004 | Weissensteiner et al. | 556/16 |
| 7,015,342 | B2 * | 3/2006 | Knochel et al. ..... | 556/14 |
| 7,094,907 | B2 * | 8/2006 | Berens ............... | 548/412 |
| 2006/0241315 | A1 * | 10/2006 | Spindler et al. ..... | 556/16 |
| 2007/0142655 | A1 * | 6/2007 | Lotz et al. .......... | 556/16 |

FOREIGN PATENT DOCUMENTS

| | | |
|---|---|---|
| DE | 100 52 391 | 5/2002 |
| EP | 0 803 510 | 10/1997 |
| EP | 0 842 140 B | 5/1998 |
| WO | 02/083695 | 10/2002 |
| WO | 03/031456 | 4/2003 |
| WO | 03/048107 | 6/2003 |
| WO | 03/076451 | 9/2003 |
| WO | 03/093285 | 11/2003 |

OTHER PUBLICATIONS

Kurt Drewelies et al., "o- and m-Phenylenebis(dichlorophosphane)-Versatile, Useful Synthetic Building Blocks", Angewandte Chemie. International Edition, Verlag Chemie. Weinheim, DE, vol. 21, No. 8, 1982, pp. 638-639, XP002192246, ISSN: 0570-0833.

(Continued)

*Primary Examiner*—Shaojia Anna Jiang
*Assistant Examiner*—Louisa Lao
(74) *Attorney, Agent, or Firm*—Wenderoth, Lind & Ponack, L.L.P.

(57) ABSTRACT

The invention relates to compounds having a structural element of formula (I) in an aromatic hydrocarbon ring, wherein: M represents —Li, —MgX$_3$, (C$_1$-C$_{18}$-Alkyl)$_3$Sn—, —ZnX$_3$ or —B(O—C$_1$-C$_4$-Alkyl)$_2$; X$_1$ and X$_2$, independent of one another, represent O or N, and C-bound hydrocarbon radicals or heterohydrocarbon radicals are bound to the free bonds of the O and N atoms; group —C=C—, together with C atoms, forms a hydrocarbon aromatic compound and represents X$_3$ Cl, Br or I. The inventive compounds are easily obtained by directly substituting the hydrogen in the ortho position to the P atom with metalation reagents. The metal atoms can then be substituted by a reactive electrophilic compound. The group —P(X$_1$—)(X$_2$—) - - - - (BH$_3$)$_{0,1}$ can then be converted into a secondary phosphine group. The inventive method enables the production of monophosphines and diphosphines even on a large scale, which are valuable ligands for metal complexes serving as catalysts for, e.g. enantioselective hydrogenations.

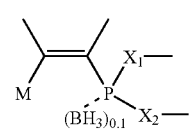

(I)

14 Claims, No Drawings

OTHER PUBLICATIONS

Michael Mehring et al., "The First Rigid O,C,O-Pincer Ligand and Its Application for the Synthesis of Penta- and Hexacoordinate Organotin(IV) Compounds", Organometallics, 17 (6), pp. 1227-1236, 1998, XP002323768, ISSN; 0276-7333.

Manfred T. Reetz et al., "New non-$C_2$-symmetric phosphine-phosphonites as ligands in asymmetric metal catalysis", Tetrahedron: Asymmetry, 10, pp. 2129-2137, 1999, XP004174097, ISSN: 0957-4166.

Konstantin W. Kottsieper et al., "Synthesis of enantiopure C1 symmetric diphosphines and phosphino-phosphonites with ortho-phenylene backbones", Tetrahedron: Asymmetry, 12, pp. 1159-1169, 2001, XP004245864, ISSN: 0957-4166.

M. Davis et al., "The Synthesis of Certain Chelating Ditertiary Phosphines", Journal of the Chemical Society, Chemical Society. Letchworth, GB, pp. 3786-3790, 1964, XP002160687, ISSN: 0368-1769.

Juan J. Almena Perea et al., "Synthesis and application of $C_2$-symmetric diamino FERRIPHOS as ligands for enantioselective Rh-catalyzed preparation of chiral α-amino acids", Tetrahedron: Asymmetry, 10, pp. 375-384, 1999, XP004158858, ISSN: 0957-4166.

* cited by examiner

METHOD FOR PRODUCING ORTHOMETALATED AND ORTHOSUBSTITUTED METALLOCENES

The present invention relates to a process for preparing metallocenes which is metalated in the ortho position relative to a secondary phosphino group containing two O—P bonds, two N—P bonds or one O—P bond and one N—P bond or a borane adduct thereof by direct replacement of the ortho hydrogen atom by means of an organolithium or organomagnesium compound and, if appropriate, subsequent transmetalation; the ortho-metalated metallocene-phosphines which can be obtained by the process; a process for preparing orthosubstituted metallocene-phosphines having a secondary phosphine group containing two O—P bonds, two N—P bonds or one O—P bond and one N—P bond by reacting a corresponding ortho-metalated metallocene-phosphine with electrophilic compounds; and intermediates obtained in this process.

Ortho-substituted aromatic monophosphines and diphosphines having secondary phosphino groups, for example compounds from the group consisting of di(sec-phosphino) ferrocenes and 1,2-di(sec-phosphino)benzenes, have been found to be valuable ligands for catalysts, in particular for the enantioselective hydrogenation of prochiral organic compounds. Ligands of this type have been widely described in the literature. Ferrocenyldiphosphines are described, for example, in Tetrahedron: Asymmetry 9 (1998), pages 2377-2407 (C. J. Richards, A. J. Locke), WO 00/37478, Angew. Chem., 114 (2002) 24, pages 4902-4905 (M. Lotz, K. Polborn, P. Knochel), EP-A1-0 564 406, EP-A1-0 612 758 and EP-A1-0 646 590. 1,2-Diphosphinobenzenes are described, for example, in EP-A1-0 592 552 and EP-A1-0 889 048.

To substitute aromatic compounds in the ortho position, aromatic compounds often contain ortho-directing substituents which are bound to the aromatic skeleton via a carbon atom, oxygen atom or nitrogen atom. Such substituents cannot be replaced under mild reaction conditions in order to produce, for example, aromatic 1,2-diphosphines in subsequent steps. Phosphino groups are therefore often introduced in or with the ortho-directing substituents in order to obtain diphosphine ligands, as has been described, inter alia, in the abovementioned literature. Aromatic ortho-diphosphines having phosphino groups bound directly to the aromatic skeleton and also other polydentate phosphine ligands which have a substituent which is not ortho-directing in the ortho position relative to the phosphine group cannot be synthesized by this route.

One method of synthesizing ferrocenyl-1,2-diphosphines having a sulfoxyl group which can be split off is described by F. Rebière in Angew. Chem. (1993), page 105. In the reaction with butyllithium, the sulfoxyl group has an ortho-directing effect and further reaction with a secondary phosphine halide gives 1-toluenesulfoxyl-2-sec-phosphinoferrocenes. The sulfoxyl group can then be replaced to give ferrocenyl-1,2-diphosphines. This synthetic method is firstly very complicated and the desired compounds are obtained only in small yields. A first problem is the preparation of the chiral and optically pure ferrocene sulfoxide which has to be carried out via ferrocenyltin compounds which can be prepared only with difficulty. When starting out from ferrocenyllithium and optically pure menthyl p-toluenesulfinate, racemization is a problem. The chiral ferrocenyl sulfoxide is obtained in an ee of only 83%. After chromatographic purification, the product has to be recrystallized twice to obtain an optically pure product (ee 99.3%, yield 49%). A second problem is the replacement of the sulfoxide group after a substituent has been introduced in the ortho position by means of ortholithiation and reaction with an electrophilic compound. The sulfoxide group is usually split off by means of t-butyllithium and the resulting ferrocenyllithiums decompose very easily and have only a very short life even at low temperatures. The process is therefore not suitable for an industrial scale.

In Angew. Chem. (1982), 94(8), page 642, K. Drewelies et al. describe the preparation of 1,2-bis(dichlorophosphino) benzene, in which the bromine atom of 1-bis(dimethylamino) phosphino-2-bromobenzene is replaced by lithium by means of reaction with butyllithium, the product is subsequently reacted with bis(dimethylamino)phosphine chloride to give 1,2-bis(dimethylamino)phosphinobenzene from which 1,2-bis(dichlorophosphino)benzene is obtained by reaction with HCl in diethyl ether. In this method, ortho substitution is forced by the presence of the bromine atom. The preparation of brominated starting materials also complicates the synthesis.

It is known from WO 03/031456A2 that 3-(dimethylamino)phosphinothiophene can be reacted with butyllithium and then reacted further without isolation of the intermediate with bis(dimethylamino)phosphine chloride to give 2,3-bis (dimethylamino)phosphinothiophene. Substitution in the ortho position is brought about by activation of the hydrogen atom in the a position relative to the S atom.

Direct metalation of unactivated hydrogen atoms in the ortho position relative to a P(III) substituent of metallocenes is not yet known. There is a need for such a synthetic method in order to be able to prepare, in particular, metallocene 1,2-diphosphines in a simpler manner on a relatively large scale, too.

It has now surprisingly been found that the unactivated hydrogen atom in the ortho position relative to the phosphino group in metallocenes can be metalated regioselectively in high yields by means of organic lithium or magnesium compounds when the phosphino group contains amino and/or oxy substituents. The reaction proceeds particularly well when borane of the formula $BH_3$ is additionally bound to the P atom. These metalated compounds can then be converted by means of many electrophilic compounds with replacement of the metal into valuable intermediates from which, in particular, ligands for homogeneous metal catalysts can be obtained by converting the phosphine group bearing amino and/or oxy substituents into a secondary phosphine group having hydrocarbon substituents in a manner known per se. Diphosphine ligands and other polydentate ligands having at least one phosphino group can be prepared significantly more economically and in higher total yields even on a relatively large scale by means of this overall process.

In metallocenes, for example ferrocenes, metalation generates planar chirality. In addition, it has surprisingly been found that the metalation proceeds highly stereoselectively when the N or 0 atoms in the phosphino group bear chiral radicals which, in particular, contain a chiral carbon atom in the a position relative to the N or 0 atoms. In this way, diastereomers are obtained directly in high optical yields by means of the synthesis, so that complicated separation operations are avoidabe. The invention firstly provides a process for preparing ferrocene, bisindenylferrocene or ruthenocene having a structural element of the formula I in the aromatic hydrocarbon ring,

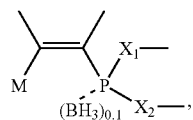
(I)

where

M is —Li, —MgX$_3$, (C$_1$-C$_{18}$-alkyl)$_3$Sn—, —ZnX$_3$ or —B(O—C$_1$-C$_4$-alkyl)$_2$, X$_1$ and X$_2$ are each, independently of one another, 0 or N and C-bonded hydrocarbon or heterohydrocarbon radicals are bound to the free bonds of the 0 or N atoms, the group —C=C— together with carbon atoms forms a hydrocarbon aromatic and X$_3$ is Cl, Br or I, which is characterized in that ferrocenes, bisindenviferrocenes or ruthenocenes having a structural element of the formula II in the aromatic ring,

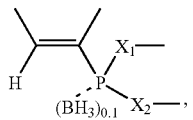
(II)

where X$_1$ and X$_2$ are as defined above and the group —C=C— together with carbon atoms forms a hydrocarbon aromatic, is reacted with at least equivalent amounts of alkyllithium, a magnesium Grignard compound or an aliphatic Li sec-amide or X$_3$Mg sec-amide, and, to prepare compounds of the formula I in which M is —MgX$_3$, (C$_1$-C$_{18}$-alkyl)$_3$Sn—, —ZnX$_3$ or —B(O—C$_1$-C$_4$-alkyl)$_2$, a lithium compound of the formula Ia,

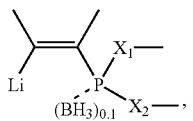
(Ia)

is reacted with at least equivalent amounts of Mg(X$_3$)$_2$, Zn(X$_3$)$_2$, (C$_1$-C$_{18}$-alkyl)$_3$SnX$_3$ or B(O—C$_1$-C$_4$-alkyl)$_3$.

Aliphatic Li sec-amide or X$_3$Mg sec-amide can be derived from secondary amines which have from 2 to 18, preferably from 2 to 12 and particularly preferably from 2 to 10, carbon atoms. Aliphatic radicals bound to the N atom can be alkyl, cycloalkyl or cycloalkylalkyl, or N-heterocyclic rings having from 4 to 12, preferably from 5 to 7, carbon atoms can be present. Examples of radicals bound to the N atom are methyl, ethyl, n-propyl, n-butyl, pentyl, hexyl, cyclopentyl, cyclohexyl and cyclohexylmethyl. Examples of N-heterocyclic rings are pyrrolidine, piperidine, morpholine, N-methylpiperazine, 2,2,6,6-tetramethylpiperidine and azanorbornane. In a preferred embodiment, the amides correspond to the formulae Li—N(C$_1$-C$_4$-alkyl)$_2$ or X$_3$Mg—N(C$_1$-C$_4$-alkyl)$_2$, where alkyl is in particular methyl.

In the case of ferrocenes, bisindenylferrocene and ruthenocenes, a structural element of the formula I can be present in one cyclopentadienyl ring or in each of the two cyclopentadienyl rings. Preferred metallocene is ferrocene.

In the formula I, M is preferably —Li or —MgX$_3$, where X$_3$ is Cl, Br or I. Particular preference is given to M being —Li.

X$_1$ and X$_2$ in the formula I are preferably N.

According to the invention, it is possible for, for example, the following hydrocarbon or heterohydrocarbon radicals to be bound to the groups X$_1$ and X$_2$:

a monovalent (hetero)hydrocarbon radical is bound to each of X$_1$ and X$_2$ or a divalent (hetero)hydrocarbon radical is bound to X$_1$ and X$_2$ when X$_1$ and X$_2$ are O;

two monovalent (hetero)hydrocarbon radicals are bound to each of X$_1$ and X$_2$ when X$_1$ and X$_2$ are N;

two divalent (hetero)hydrocarbon radicals are bound to each of X$_1$ and X$_2$ when X$_1$ and X$_2$ are N, with the divalent (hetero)hydrocarbon radicals being able to be bridged by a bond, methylene or ethylene;

a divalent (hetero)hydrocarbon radical is bound to X$_1$ and two monovalent radicals are bound to X$_2$ when X$_1$ and X$_2$ are N, with a monovalent radical being methylene or ethylene bound to the divalent (hetero)hydrocarbon radical;

a monovalent (hetero)hydrocarbon radical is bound to each of X$_1$ and X$_2$ and a divalent (hetero)hydrocarbon radical is bound to each of X$_1$ and X$_2$ when X$_1$ and X$_2$ are N;

two monovalent (hetero)hydrocarbon radicals are bound to X$_1$ and a divalent (hetero)hydrocarbon radical is bound to X$_2$ when X$_1$ and X$_2$ are N;

two divalent (hetero)hydrocarbon radicals are bound to each of X$_1$ and X$_2$ when X$_1$ and X$_2$ are N;

X$_1$ is O and a monovalent (hetero)hydrocarbon radical is bound to X$_1$ and X$_2$ is N and two monovalent (hetero)hydrocarbon radicals or a divalent (hetero)hydrocarbon radical are/is bound to X$_2$;

X$_1$ is O and X$_2$ is N and a divalent (hetero)hydrocarbon radical is bound to X$_1$ and X$_2$ and a monovalent (hetero) hydrocarbon radical is bound to X$_2$;

a divalent, aromatic 1,1'-(hetero)hydrocarbon radical is bound when X$_1$ and X$_2$ are O; or a divalent, aromatic 1,1'-(hetero)hydrocarbon radical is bound to X$_1$ and X$_2$ and a monovalent (hetero)hydrocarbon radical is bound to each of X$_1$ and X$_2$ when X$_1$ and X$_2$ are N.

Hydrocarbon or heterohydrocarbon radicals which are C-bonded to X$_1$ and X$_2$ can be a) saturated or unsaturated, straight-chain, branched or cyclic and monovalent radicals, with two monovalent radicals being bound to X$_1$ and X$_2$ when the latter are N;

b) saturated, unsaturated, straight-chain, branched and/or cyclic or bicyclic divalent radicals which are bound to X$_1$ and/or X$_2$ when X$_1$ and X$_2$ are N and form a 4- to 7-membered ring, or c) saturated, unsaturated, straight-chain, branched and/or cyclic or bicyclic divalent radicals which bridge an O atom and an N atom or form a single or double bridge between two N atoms and together with the —X$_1$—P—X$_2$— group form a 5- to 7-membered ring.

Heterohydrocarbon radicals can contain heteroatoms selected from the group consisting of O, S and N(C$_1$-C$_4$-alkyl). The number of heteroatoms is preferably from 1 to 4, more preferably from 1 to 3 and particularly preferably 1 or 2. The hydrocarbon or heterohydrocarbon radicals can contain from 1 to 18, preferably from 1 to 12 and particularly preferably from 1 to 8, carbon atoms and, if appropriate, heteroatoms. The radicals can be monosubstituted or polysubstituted, preferably monosubstituted to trisubstituted or monosubstituted or disubstituted, for example by phenyl, phenoxy, benzyl, benzyloxy, C$_1$-C$_4$-alkylphenyl, C$_1$-C$_4$-alkylphenoxy, C$_1$-C$_4$-alkylbenzyl, C$_1$-C$_4$-alkylbenzyloxy, C$_1$-C$_4$-alkoxyphenyl, C$_1$-C$_4$-alkoxyphenoxy, C$_1$-C$_4$-alkoxybenzyl, $C_1$-$C_4$-alkoxybenzyloxy, $C_1$-$C_4$-alkylthiophenyl, $C_1$-$C_4$-alkylthiophenoxy, $C_1$-$C_4$-alkylthiobenzyl, $C_1$-$C_4$-alkylthiobenzyloxy, di($C_1$-$C_4$-alkyl)aminophenyl, di($C_1$-$C_4$-alkyl)aminophenoxy, cyclohexyl, cyclopentyl, $C_1$-$C_4$-alkylcyclohexyl, $C_1$-$C_4$-alkylcyclopentyl, $C_1$-$C_4$-alkoxycyclohexyl, $C_1$-$C_4$-alkoxycyclopentyl, fluorine, $C_1$-$C_4$-alkyl, $C_1$-$C_4$-fluoroalkyl, $C_1$-$C_4$-alkoxy, $C_1$-$C_4$-alkylthio, di($C_1$-$C_4$-alkyl)amino, $C_1$-$C_4$-alkoxy-$C_1$-$C_4$-alkyl, $C_1$-$C_4$-alkylthio-$C_1$-$C_4$-alkyl, or di($C_1$-$C_4$-alkyl)amino-$C_1$-$C_4$-alkyl. Substitution in the α or β positions relative to the groups $X_1$ and $X_2$ is preferred insofar as the radical has chiral carbon atoms which can result in optical induction in the metalation and subsequent reactions. Some specific substituents are methyl, ethyl, n- and i-propyl, n-, i- and t-butyl, trifluoromethyl, methoxy, ethoxy, propoxy, i-propoxy, butoxy, i-butoxy, t-butoxy, methylthio, ethylthio, dimethylamino, diethylamino, phenyl, phenoxy, methoxyphenyl and methoxyphenoxy.

Hydrocarbon or heterohydrocarbon radicals which are C-bonded to $X_1$ and $X_2$ can be monovalent radicals such as unsubstituted or substituted $C_1$-$C_{18}$-, preferably $C_1$-$C_{12}$- and particularly preferably $C_1$-$C_8$-(hetero)alkyl; unsubstituted or substituted $C_2$-$C_{18}$-, preferably $C_2$-$C_{12}$- and particularly preferably $C_3$-$C_8$-(hetero)alkenyl; unsubstituted or substituted $C_3$-$C_{12}$- and preferably $C_3$-$C_8$-(hetero)cycloalkyl, unsubstituted or substituted $C_3$-$C_{12}$- and preferably $C_3$-$C_8$-(hetero)cycloalkenyl, unsubstituted or substituted $C_3$-$C_{12}$- and preferably $C_3$-$C_8$-(hetero)cycloalkyl-$C_1$-$C_4$-alkyl, substituted or unsubstituted $C_3$-$C_{12}$- and preferably $C_3$-$C_8$-(hetero)cycloalkenyl-$C_1$-$C_4$-alkyl, substituted or unsubstituted $C_6$-$C_{14}$-(hetero)aryl, and $C_6$-$C_{14}$-(hetero)aryl-$C_1$-$C_4$-alkyl. Preference is given to saturated and aromatic hydrocarbon or heterohydrocarbon radicals.

Monovalent hydrocarbon radicals can be linear or branched $C_1$-$C_{12}$-alkyl, preferably $C_1$-$C_8$-alkyl and particularly preferably $C_1$-$C_4$-alkyl, $C_3$-$C_8$- and preferably $C_4$-$C_6$-cycloalkyl, $C_3$-$C_8$-cycloalkyl- and preferably $C_4$-$C_6$-cycloalkyl-methyl or -ethyl, $C_6$-$C_{14}$- and preferably $C_6$-$C_{10}$-aryl, $C_7$-$C_{15}$-aralkyl and preferably $C_7$-$C_{11}$-aralkyl. Some specific examples are methyl, ethyl, n- and i-propyl, n-butyl, pentyl, hexyl, heptyl, octyl, cyclopropyl, cyclobutyl, cyclopentyl, cyclohexyl, cycloheptyl, cyclooctyl, cyclobutylmethyl, cyclopentylmethyl, cyclohexylmethyl, cyclobutylethyl, cyclopentylethyl, cyclohexylethyl, phenyl, naphthyl, benzyl and phenylethyl. If chiral induction is to be achieved, for example in the case of ferrocenes, the hydrocarbon radicals are then preferably substituted in the a- and/or , position relative to $X_1$ and/or $X_2$, for example by $C_1$-$C_4$-alkyl, $C_1$-$C_4$-alkoxy, ($C_1$-$C_4$-alkyl)$_2$N—, $C_1$-$C_4$-alkoxymethyl, $C_1$-$C_4$-alkoxyethyl, ($C_1$-$C_4$-alkyl)$_2$N-methyl or -ethyl, phenyl, methylphenyl, methoxyphenyl, phenoxy, 2-anisyl, benzyl or benzyloxy.

Some examples of monovalent heterohydrocarbon radicals are $C_1$-$C_8$-alkoxy-$C_2$-$C_4$-alkyl, ($C_1$-$C_4$-alkyl)$_2$N-$C_2$-$C_4$-alkyl, $C_5$-$C_7$-cycloalkoxy-$C_2$-$C_4$-alkyl, $C_4$-$C_{10}$-(hetero)aryloxy-$C_2$-$C_4$-alkyl, $C_4$-$C_7$-heterocycloalkyl-$C_1$-$C_4$-alkyl, $C_4$-$C_{10}$-heteroaryl-$C_1$-$C_4$-alkyl. Some specific examples are methoxyethyl, ethoxyethyl, dimethylaminoethyl, diethylaminoethyl, cyclohexyloxyethyl, phenoxyethyl, N-methylmorpholinylmethyl or N-methylmorpholinylethyl, N-methylpiperidinylmethyl or N-methylpiperidinylethyl, pyridinylmethyl or pyridinylethyl and pyrrolidinylmethyl or pyrrolidinylethyl.

Divalent hydrocarbon radicals which are bound to each of $X_1$ and $X_2$ when $X_1$ and $X_2$ are each N and together with the N atom form a 4- to 7-membered ring can have from 2 to 8, preferably from 2 to 6 and more preferably from 2 to 4, carbon atoms and are preferably linear or branched, unsubstituted or substituted alkylene onto which aliphatic or aromatic rings may be fused. The hydrocarbon chain can be interrupted by O atoms and/or —N($C_1$-$C_4$-alkyl). Examples of divalent hydrocarbon radicals are trimethylene, tetramethylene, pentamethylene, —$CH_2$)$_2$—O—($CH_2$)$_2$—, —($CH_2$)$_2$—N($CH_3$)—($CH_2$)$_2$—. Divalent hydrocarbon radicals form a heterocyclic ring with the atoms to which they are bound. If chiral induction is to be achieved, for example in the case of ferrocenes, the hydrocarbon radicals are then preferably substituted in the α- or β position relative to $X_1$ and/or $X_2$, for example by $C_1$-$C_4$-alkyl, $C_1$-$C_4$-alkoxy, $C_1$-$C_4$-alkoxymethyl, $C_1$-$C_4$-alkoxyethyl, —N($C_1$-$C_4$-alkyl), ($C_1$-$C_4$-alkyl)$_2$N-methyl or -ethyl, phenyl, 2-anisyl or benzyl. If both N atoms are bridged by two divalent radicals, these radicals are derived from cyclic diamines, for example piperazine.

Divalent hydrocarbon radicals which are bound to $X_1$ and $X_2$ when $X_1$ and $X_2$ are each N are preferably derived from 1,2- or 1,3-diamines, with an amino group being able to be part of a ring. The divalent hydrocarbon radicals can be linear or branched 1,2- or 1,3-$C_2$-$C_{12}$-alkylene, preferably 1,2- or 1,3-$C_2$-$C_8$-alkylene and particularly preferably 1,2- or 1,3-$C_2$-$C_4$-alkylene, 1,2- or 1,3-$C_3$-$C_8$- and preferably 1,2- or 1,3-$C_4$-$C_6$-cycloalkylene, 1-$C_3$-$C_8$-cycloalkyl- and preferably 1-$C_4$-$C_6$-cycloalkyl-2-methylene or -ethylene, $C_6$-$Cl_4$- and preferably 1,2-$C_6$-$C_{10}$-arylene and $C_6$-$C_{10}$-aralk-1-yl-2-methylene. Some specific examples are ethylene, n- and i-propylene, n- or i-butylene, cyclopropyl-1,2-ene, cyclobutyl-1,2-ene, cyclopentyl-1,2-ene, cyclohexyl-1,2-ene, cycloheptyl-1,2-ene, cyclooctyl-1,2-ene, cyclobut-1-yl-2-methylene, cyclopent-1-yl-2-methylene, cyclohex-1-yl-2-methylene, cyclobut-1-yl-2-ethylene, cyclopent-1-yl-2-ethylene, cyclohex-1-yl-2-ethylene, 1,2-phenylene, 1,2-naphthylene, phen-1-yl-2-methylene and phen-1-yl-2-ethylene. If chiral induction is to be achieved, for example in the case of ferrocenes, the hydrocarbon radicals are then preferably substituted in the α and/or β position relative to $X_1$ and/or $X_2$, for example by $C_1$-$C_4$-alkyl, $C_1$-$C_4$-alkoxymethyl, $C_1$-$C_4$-alkoxyethyl, —N($C_1$-$C_4$-alkyl), ($C_1$-$C_4$-alkyl)$_2$N-methyl or -ethyl, phenyl, 2-anisyl or benzyl.

Divalent hydrocarbon radicals which are bound to $X_1$ and $X_2$ when $X_1$ and $X_2$ are each N can also be 1,1'-biphenylene, 1,1'-binaphthylene and 1,1'-bispyridine.

Preferred phosphine groups in the formula I are ones in which an N-heterocycloalkyl which is substituted in the a position relative to the N atom by $C_1$-$C_4$-alkyl, $C_1$-$C_4$-alkoxymethyl or $C_1$-$C_4$-alkoxyethyl and has a total of 4, 5, 6 or 7 ring atoms or a 1,2-diamino-$C_4$-$C_7$-cycloalkyl is bound to the phosphorus atom or in which an N,N'-substituted diamine is bound to the phosphorus atom and together with the P atom forms an N—P—N-heterocycloaliphatic ring having from 4 to 7 ring atoms and further substituents may be bound to the carbon atoms. Suitable open-chain substituents on the phosphorus atom are, for example, —N($C_1$-$C_4$-alkyl)-$C_2$-$C_4$-alkylene-N($C_1$-$C_4$-alkyl)$_2$.

Particularly preferred phosphino groups in the formula I correspond to the formulae:

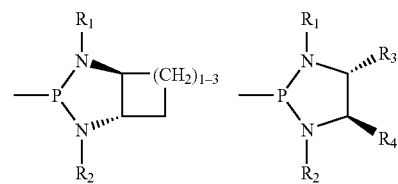

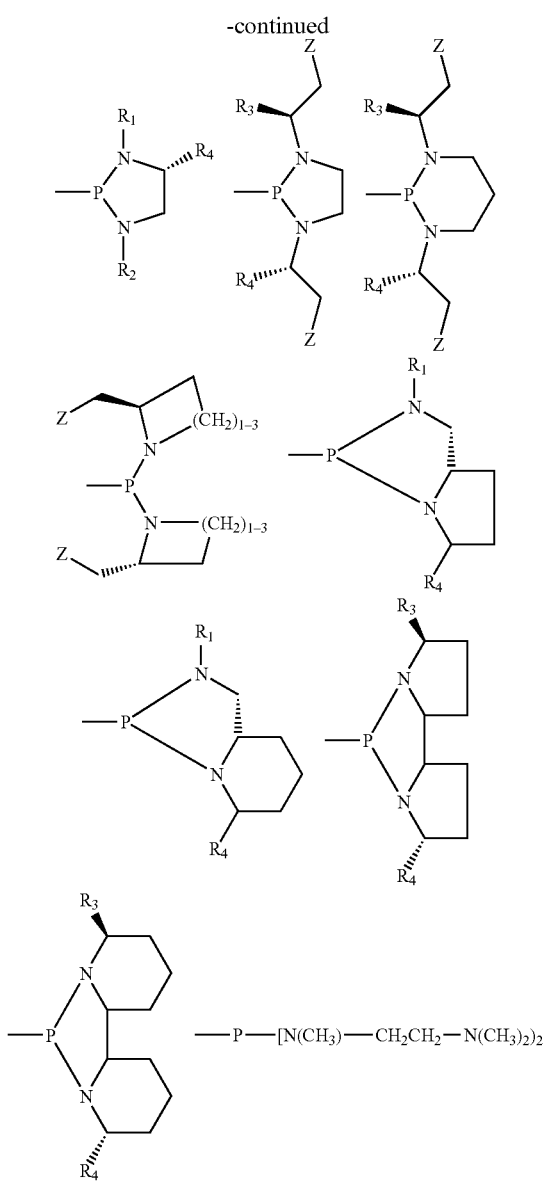

where

R₁ and R₂ are identical or different and preferably identical and are each $C_1$-$C_4$-alkyl, $C_1$-$C_4$-alkoxyethyl, $(C_1$-$C_4$-alkyl$)_2$N-ethyl, R₃ and R₄ are identical or different and preferably identical and are each H, $C_1$-$C_4$-alkyl, phenyl or methylphenyl and Z is H, $C_1$-$C_4$-alkyl, $C_1$-$C_4$-alkoxy, $C_1$-$C_4$-alkylthio, -N$(C_1$-$C_4$-alkyl$)_2$, phenyl, phenoxy, methoxyphenyl or methoxyphenoxy.

Some further examples of Z are methyl, ethyl, methoxy, ethoxy, methylthio and dimethylamino.

The metalation of metallocenes involves known reactions which are described, for example, by M. Schlosser (Editor) in Organometallics in Synthesis, John Wiley & Sons (1994) or in Jonathan Clayden Organolithiums: Selectivity for Synthesis (Tetrahedron Organic Chemistry Series), Pergamon Press (2002).

For the purposes of the invention, the expression at least equivalent amounts means the use of from 1 to 1.2 equivalents of a magnesium Grignard compound or an aliphatic Li sec-amide or X₃Mg sec-amide per reactive =CH— group of a metallocene, for example from 1 to 1.2 equivalents of Mg $(X_3)_2$, Zn$(X_3)_2$, $(C_1$-$C_{18}$-alkyl$)_3$SnX₃ or B(O—$C_1$-$C_4$-alkyl$)_3$ per =C—Li group in a compound of the formula Ia.

The reaction is advantageously carried out at low temperatures, for example from 20 to When ferrocenes having a structural element of the formula II are used, metalation in the second cyclopentadienyl ring can be achieved simultaneously if at least two equivalents of a metalation reagent are used. −100° C., preferably from 0 to −80° C. The reaction time is from about 2 to 5 hours. The reaction is advantageously carried out under an inert protective gas, for example nitrogen or noble gases such as argon.

The reaction is advantageously carried out in the presence of inert solvents. Such solvents can be used either alone or as a combination of at least two solvents. Examples of solvents are aliphatic, cycloaliphatic and aromatic hydrocarbons and also open-chain or cyclic ethers. Specific examples are petroleum ether, pentane, hexane, cyclohexane, methylcyclohexane, benzene, toluene, xylene, diethyl ether, dibutyl ether, tert-butyl methyl ether, ethylene glycol dimethyl or diethyl ether, tetrahydrofuran and dioxane.

A transmetalation of the compounds of the formula Ia can be carried out directly subsequent to the preparation of the lithium compound without isolation of the latter. For this purpose, the metalation reagent is added to the reaction mixture, with the above-described reaction conditions are being able to be employed. It is also possible to use magnesium Grigard compounds as metalation reagent in order to prepare compounds bearing the group -MgX₃.

Compounds of the formula II are known or can be prepared by methods which are known or analogous to known methods. For example, monolithiated metallocenes are used as starting materials and are reacted with monohalophosphines of the formula X₃P(X₁-)X₂-, where X₃ is preferably Cl or Br, X₁ and X₂ are $_O$ or N and a hydrocarbon radical is bound to the free bonds of X₁- and X₂-. Subsequent to the reaction, the borane BH₃, whose presence is desirable, can be introduced in a manner known per se, for example by reacting the reaction mixture with a borane complex such as BH₃·S(CH₃)₂. Monohalophosphines of the formula X₃P(X₁-)X₂- are known or can be obtained in a manner known per se from phosphorus trichloride by reaction with alcohols, amines, amino alcohols or diamines.

The compounds of the formula I are colored solids which precipitate from the reaction mixture and can be filtered off and then purified if necessary. Storage of the compounds is advantageously carried out in a suspension of the compounds in a medium in which they are not soluble, for example hydrocarbons or ethers (as described above as reaction solvents). The compounds of the formula I can, however, also be reacted further directly after their preparation in their reaction mixture. The compounds of the formula I are valuable intermediates for the preparation of metallocenes substituted in the ortho position.

The invention further provides the compounds of the formula I, including the abovementioned embodiments and preferences.

In a preferred embodiment, the compounds of the formula I are compounds having a ferrocene skeleton, in particular those corresponding to the formula Ib or Ic,

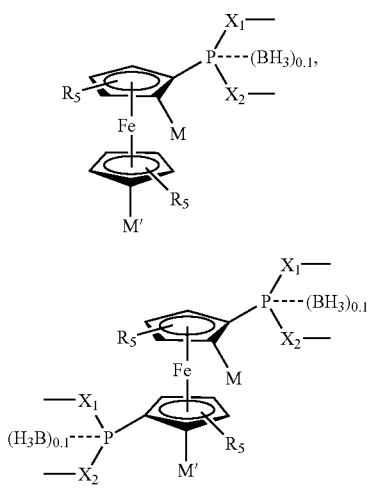

where
R$_5$ is C$_1$-C$_4$-alkyl and preferably a hydrogen atom,
M is —MgCl, —MgBr and preferably Li,
M' is H, —MgCl, —MgBr or Li and
X$_1$ and X$_2$ and also the radicals bound to free bonds of X$_1$ and X$_2$ have the abovementioned meanings, including the abovementioned advantageous embodiments and preferences.

The invention also provides a process for preparing ferrocene, bisindenylferrocene or ruthenocene having a structural element of the formula III in the aromatic ring,

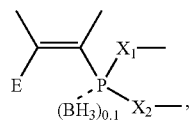
(III)

where
X$_1$ and X$_2$ and also the radicals bound to free bonds have the abovementioned meanings and
E is the radical of a reactive, electrophilic compound which is able to replace a metal bound to ferrocene, bisindenylferrocene or ruthenocene or a bound metal group, which is characterized in that a compound having a structural element of the formula I,

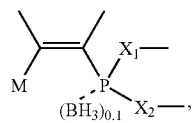
(I)

where
M, X$_1$ and X$_2$ and the radicals bound to free bonds have the abovementioned meanings, is reacted with at least equivalent amounts of a reactive electrophilic compound.

The abovementioned embodiments and above-described preferences apply to M, X$_1$ and X$_2$ and also the radicals bound to free bonds.

For the purposes of the invention, a reactive eletrophilic compound is any reagent which can be bound to replace M in the formula I. Catalysts may be used concomitantly and monovalent radicals E may be formed only in a subsequent step after addition of the reagent (for example hydrolysis). Such reagents are widely known in organometallic chemistry and described for metalated aromatic hydrocarbons, cf., for example, V. Snieckus, Chem. Rev., 90(1990) 879-933; Manfred Schlosser (Editor), Organometallics in Synthesis, A. Manual, second Edition, John Wiley & Sons, LTD, (2002); Organolithiums: Selectivity for Synthesis (Tetrahedron Organic Chemistry Series) Chapter 6 & 7, Pergamon Press (2002) and Kagan H.B., et al., J. Org. Chem., 62(1997)6733-45(for example for the introduction of a selection of possible electrophilic commpounds on metalated ferrocenes).

Examples of reactive electrophilic compounds are:
halogens (Cl$_2$, Br$_2$, I$_2$), interhalogens (Cl—Br, Cl—I) and aliphatic, perhalogenated hydrocarbons (Cl$_3$C—CCl$_3$ or BrF$_2$C—CF$_2$Br) for the introduction of Cl, Br or I;

CO$_2$ for the introduction of the carboxyl group —CO$_2$H;

chlorocarbonates or bromocarbonates [Cl—C(O)—OR] for introduction of a carboxylate group, where R is hydrogen or a hydrocarbon radical (alkyl, cycloalkyl, cycloalkylalkyl, aryl, aralkyl, heteroaryl, heteroaralkyl) which has from 1 to 18, preferably from 1 to 12 and particularly preferably from 1 to 8, carbon atoms and is unsubstituted or substituted by inert substituents such as sec-phosphino, di(C$_1$-C$_8$-alkyl)$_2$N—, —C(O)—OC$_1$-C$_8$-alkyl or —OC$_1$-C$_8$-alkyl (inert substituents include reactive groups such as Cl, Br or I if groups which are more reactive toward a metal or a metal group in compounds of the formula I, for example—CHO, are simultaneously present, or if Cl and Br, Cl and I or Br and I are simultaneously bound in a preferably aromatic hydrocarbon radical);

di(C$_1$-C$_4$-alkyl)formamides, for example dimethylformamide or diethylformamide, for introduction of the group-CH(O);

di(C$_1$-C$_4$-alkyl)carboxamides for introduction of a —C(O)—R group;

aldehydes which may be unsubstituted or substituted by sec-phosphino in the group R for introduction of a —CH(OH)—R group;

symmetrical or unsymmetrical ketones which may be unsubstituted or substituted by sec-phosphino in the group R or R' for introduction of a —C(OH)RR' group, where R' has, independently, one of the meanings of R or R and R' together form a cycloaliphatic ring having from 3 to 8 ring atoms;

epoxides for introduction of a —C—C—OH group in which the carbon atoms may be substituted by H or R; imines R—CH=N—R' for introduction of the group —CH(R)—NHR', where R' has, independently, one of the meanings of R, or R and R' together form a cycloaliphatic ring having from 3 to 8 ring atoms; R and R' are not simultaneously hydrogen;

imines R—C(R")=N—R' for introduction of the group —C(R)(R")—NHR', where R' independently has one of the meanings of R, or R and R' together form a cycloaliphatic ring having from 3 to 8 ring atoms, R" independently has one of the meanings of R, or R and R" together form a cycloaliphatic ring having from 3 to 8 ring atoms;

hydrocarbon and heterohydrocarbon monohalides, in particular chlorides, bromides and iodides, for introduction of hydrocarbon and heterohydrocarbon radicals (for example C$_1$-C$_{18}$-alkyl, C$_6$-C$_{14}$-aryl, C$_7$-C$_{14}$-aralkyl);

halohydrocarbons and haloheterohydrocarbons having halogen atoms of differing reactivity, in particular combinations of chlorine with bromine or iodine, bromine with iodine or two bromine or iodine atoms in the case of steric hindrance of an intermediate formed, for introducing hydrocarbon and heterohydrocarbon radicals (for example $C_1$-$C_{18}$-alkyl, $C_6$-$C_{14}$-aryl, $C_7$-$C_{14}$-aralkyl);

alkenyl halides, in particular chlorides, bromides and iodides, for introducing alkenyl groups such as allyl and vinyl;

tri($C_1$-$C_8$-alkyl)silylhalides (chlorides, bromides) for introduction of the group tri($C_1$-$C_8$-alkyl)Si—;

di($C_1$-$C_8$-alkyl)silyldihalides (chlorides, bromides) for introduction of the divalent group —($C_1$-$C_8$-alkyl)$_2$Si— to which two radicals of the formula I are bound (in place of M);

sec-phosphine monohalides (chlorides, bromides) for introduction of sec-phosphino groups such as diphenylphosphino, di(methylphenyl)phosphino, dicyclohexylphosphino and di-t-butylphosphino;

di(sec-amino)phosphine monohalides (chlorides, bromides) for introduction of di(sec-amino)phosphino groups such as di(dimethylamino)phosphino, di(diethylamino)phosphino, N,N-diethylcyclohexylenediaminophosphino;

phosphoric ester monohalides (chlorides, bromides) for introduction of phosphonic ester groups such as $(CH_3O)_2(O)P$—, $(C_2H_5O)(O)P$—, $(cyclohexylO)_2(O)P$—, (ethylenedioxyl)(O)P—;

phosphorous ester monohalides (chlorides, bromides) for introduction of phosphorous ester groups such as $(CH_3O)_2P$—, $(C_2H_5O)P$—, $(cyclohexylO)_2P$—, (ethylenedioxyl)P—;

phosphine dihalides such as $RPCl_2$ or $RPBr_2$ for introduction of the divalent group —P(R)— to which two radicals of the formula I are bound (in place of M);

sec-arsine monohalides (chlorides, bromides) for introduction of sec-arsino groups such as diphenylarsino, di(methylphenyl)arsino, dicyclohexylarsino and di-t-butylarsino; arsine dihalides, for example $RAsCl_2$ or $RAsBr_2$ for introduction of the divalent group —As(R)— to which two radicals of the formula I are bound (in place of M);

organic disulfides R—SS—R for introduction of the group —SR;

sulfur ($S_8$) for introduction of the group —SH; and substituted or unsubstituted ferrocenyl monohalides (chlorides, bromides, iodides).

For the purposes of the invention, the expression at least equivalent amounts means the use of from 1 to 1.2 equivalents of reactive electrophilic compound per reactive =CM— group in an aromatic compound. However, a distinct excess of up to 2.5 equivalents can also be used.

The isolation of the compounds of the formula III can be carried out by methods known per se, for example extraction, filtration and distillation. After isolation, the compounds can be purified, for example by distillation, recrystallization or by chromatographic methods.

It has surprisingly been found that in the case of compounds of the formula I which have a metallocene skeleton, in particular a ferrocene skeleton, and, particularly when M is Li and the compounds have planar chirality, optical induction can obviously be achieved even in the metalation when a hydrocarbon radical having at least one chiral carbon atom is bound to at least one of the groups $X_1$ and $X_2$, preferably so that the chiral carbon atom is present in the α or β position relative to the O and/or N atoms. In this case, the introduction of electrophilic, reactive compounds results in predominant formation of one optical isomer, with the content of one diastereomer being able to be, for example, at least 70% and preferably at least 80% or more. Pure diastereomers can be obtained in a particularly simple manner at this stage using known separation processes such as recrystallization or chromatography.

The radical E of the electrophilic, reactive compound in compounds of the formula III can contain a chiral carbon atom which is bound to a carbon atom of the cyclopentadienyl ring. Such radicals are formed from prochiral electrophilic and reactive compounds, for example aldehydes and ketones. It has surprisingly been found that, particularly in the case of compounds having metallocene skeletons, preferably ferrocene skeletons, and having planar chirality and chirality at the carbon atom, the presence of C-chiral hydrocarbon radicals (preferably having a chiral carbon atom in the a position relative to the O and/or N atoms) bound to at least one of the groups $X_1$ and $X_2$, leads to very high diastereoselectivity in respect of the planar chirality and, in addition, even to a significant diastereoselectivity in respect of the chirality at the carbon atom. When prochiral electrophilic compounds are introduced, essentially only one pair of diastereomers in respect of the planar chirality among four possible diastereomers is formed, and it is often also observed that one diastereomer of the diastereomeric pair is preferentially formed. Pure diastereomers can, if necessary at all, then easily be obtained at this stage (chiral radicals on groups $X_1$ and $X_2$) by separation by means of recrystallization or in particular chromatographic methods.

The invention further provides metallocenes from the group consisting of ferrocene, bisindenylferrocene and nuthenocene having a structural element of the formula III in one or both cyclopentadienyl rings,

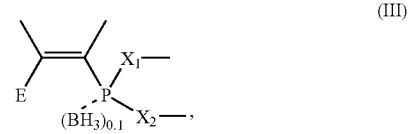

where

E, $X_1$ and $X_2$ and hydrocarbon radicals bound to the free bonds of the groups $X_1$ and $X_2$ have the abovementioned meanings, including the advantageous embodiments and preferences.

Preferred metallocenes are those which correspond to the formula IV,

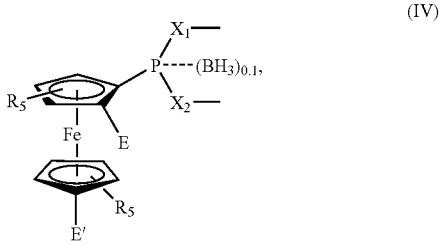

where

E' is H or has one of the meanings of E; and $R_5$, E, $X_1$ and $X_2$ and hydrocarbon radicals bound to the free bonds of the groups $X_1$ and $X_2$ have the abovementioned meanings, including the advantageous embodiments and preferences.

$R_5$ is preferably hydrogen. E is preferably —$PH_2$, —$PCl_2$, —$PBr_2$, sec-phosphino, ortho-chlorophenyl or ortho-bromophenyl or a benzyl radical of the formula

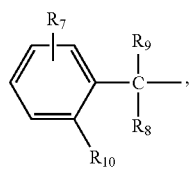

where
$R_7$ is $C_1$-$C_4$-alkyl or $C_1$-$C_4$-alkoxy and preferably a hydrogen atom,
$R_8$ is $C_1$-$C_4$-alkyl, hydroxy, $C_1$-$C_4$-alkoxy, $C_1$-$C_8$-acyloxy or sec-amino,
$R_9$ is $C_1$-$C_6$-alkyl and preferably a hydrogen atom and
$R_{10}$ is Cl, Br or I or sec-phosphino, or
the group —$CR_8R_9$— represents a direct bond and $R_{10}$ is Br or I.

Compounds in which $R_8$ is $C_1$-$C_4$-alkoxy, $C_1$-$C_8$-acyloxy or sec-amino are obtainable by etherification or esterification of the hydroxyl group $R_8$ or replacement of an acyloxy group $R_8$ by sec-amino.

When $R_8$ is sec-amino, it preferably contains from 2 to 12 and particularly preferably from 2 to 6 carbon atoms. Some examples are dimethylamino, diethylamino, methylethylamino, di-n-propylamino, di-n-butylamino, morpholino, piperidinyl and pyrrolidinyl. When $R_8$ is alkoxy, it can be methoxy, ethoxy, n-propoxy or n-butoxy. When $R_8$ is acyloxy, the radical is preferably derived from carboxylic acids. It can be acetyloxy, propanoyloxy, butanoyloxy, cyclohexanoyloxy, benzoyloxy or toluoyloxy. When R8 is alkyl, it can be, for example, methyl, ethyl, n-propyl or n-butyl.

Further preferred metallocenes are those corresponding to the formula IVa,

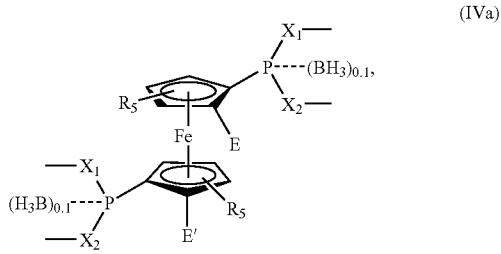

(IVa)

where
E' is H or independently has one of the meanings of E; and
$R_5$, E, $X_1$ and $X_2$ and hydrocarbon radicals bound to the free bonds of the groups $X_1$ and $X_2$ have the abovementioned meanings, including the advantageous embodiments and preferences.

$R_5$ is preferably hydrogen. E is preferably a hydrocarbon radical having a chiral carbon atom which is bound to the cyclopentadienyl ring. The chiral hydrocarbon radical having a chiral carbon atom preferably corresponds to the formula

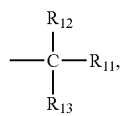

where
$R_{12}$ is hydrogen, $C_1$-$C_8$-alkyl and preferably $C_1$-$C_4$-alkyl, unsubstituted or $C_1$-$C_4$-alkyl- or $C_1$-$C_4$-alkoxy-substituted $C_4$-$C_8$-cycloalkyl or unsubstituted or $C_1$-$C_4$-alkyl- or $C_1$-$C_4$-alkoxy-substituted phenyl,
$R_{13}$ independently has one of the meanings of $R_{12}$ and Compounds of the formula III having a structural element can be converted in a known manner into monophosphines which can be used, for example, as monodentate ligands. Such monophosphines having structural elements of the formula V in one also in two aromatic hydrocarbon rings, of ferrocene, bisindenylferrocene or ruthenocene.

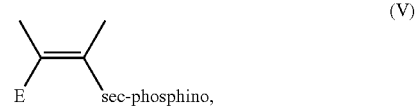

(V)

are obtained by
a) removing any borane group present from ferrocene, bisindenylferrocene or ruthenocene having a structural element of the formula III, then splitting off the radicals (hetero)hydrocarbon-$X_1$, (hetero)hydrocarbon-$X_2$ or $X_1$-(hetero)hydrocarbon-$X_2$ to form a —$PCl_2$ group or —$PBr_2$ group and then replacing the Cl or Br atoms by a hydrocarbon radical by means of an organometallic compound (Grignard reagent) to form the sec-phosphino group, or
b) splitting off the radicals (hetero)hydrocarbon-$X_1$, (hetero)hydrocarbon-$X_2$ or $X_1$-(hetero)hydrocarbon-$X_2$ to form a —$PCl_2$ group or —$PBr_2$ group and then replacing the Cl or Br atoms by a hydrocarbon radical by means of an organometallic compound (Grignard reagent) to form the sec-phosphino group and then removing the borane group.

The removal of the borane group only in the last reaction step offers the advantage that reaction-sensitive groups remain protected.

The borane group can be split off by, for example, adding reagents such as secondary amines having $C_1$-$C_4$-alkyl groups, morpholine, 1,8diazabicyclo[5,4.0]undec-7-ene (DBU), 1,4-diazabicyclo[2.2.2]octane to the dissolved compound of the formula III, sufficiently long stirring at temperatures of from 20 to 70° C. and removing the volatile constituents, advantageously under reduced pressure. Methods of removing borane are described, for example, by M. Ohff et al. in Synthesis (1998), page 1391.

The formation of —$PCl_2$ or —$PBr_2$ groups is likewise known and is described, for example, by A. Longeau et al. in Tetrahedron: Asymmetry, 8 (1997), pages 987-990. Reagents used are advantageously organic solutions of HCl or HBr in, for example, ethers, which are added at low temperatures (for example from –20 to 30° C.) to the dissolved compounds of the formula III with or without borane group.

The Grignard reagents can be mono- or di-Li-, —ClMg-, —BrMg- or —IMg-hydrocarbons which are generally added in excess, for example up to 5 equivalents per halogen atom. The reaction is carried out in solution, with solvents as mentioned above for the metalation being able to be used. The reaction can be carried out at temperatures of from –80 to 80° C.

—$PCl_2$ or —$PBr_2$ groups can be hydrogenated in a manner known per se, for example by means of Li(AlH$_4$), and the phosphino group can then be converted into a cyclic, secondary phosphino group by means of, for example, cyclic sulfates such as butylene or propylene sulfate. The monophosphines can be isolated using methods as described above.

The secondary phosphino group can bear two identical or two different hydrocarbon radicals, or the two hydrocarbon radicals can form a 3- to 8-membered ring with the P atom. The phosphino group preferably has two identical hydrocarbon radicals. The hydrocarbon radicals can be unsubstituted or substituted and can have from 1 to 22 and preferably from 1 to 12 carbon atoms. A preferred sec-phosphino group is one in which the phosphino group bears two identical or different radicals selected from the group consisting of linear or branched $C_1$-$C_{12}$-alkyl; unsubstituted or $C_1$-$C_6$-alkyl- or $C_1$-$C_6$-alkoxy-substituted $C_5$-$C_{12}$-cycloalkyl or $C_5$-$C_{12}$-cycloalkyl-$CH_2$—; phenyl or benzyl; and phenyl or benzyl substituted by halogen (for example F, Cl and Br), $C_1$-$C_6$-alkyl, $C_1$-$C_6$-haloalkyl (for example trifluoromethyl), $C_1$-$C_6$-alkoxy, $C_1$-$C_6$-haloalkoxy (for example trifluoromethoxy), $(C_6H_5)_3Si$, $(C_1$-$C_{12}$-alkyl$)_3Si$, sec-amino or —$CO_2$—$C_1$-$C_6$-alkyl (for example —$CO_2CH_3$).

The two radicals in the phosphino group can also together form unsubstituted or halogen-, $C_1$-$C_6$-alkyl- or $C_1$-$C_6$-alkoxy-substituted dimethylene, trimethylene, tetramethylene or pentamethylene. The substituents are preferably located in the two ortho positions relative to the P atom.

The phosphino groups can also be groups of the formula

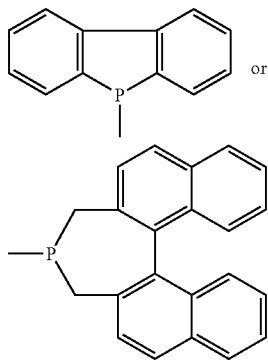

where the phenyl rings are unsubstituted or substituted by $C_1$-$C_4$-alkyl or $C_1$-$C_4$-alkoxy.

Examples of secondary phosphino groups in which the two hydrocarbon radicals form a 3- to 8-membered ring with the P atom are, in particular, those of the formula

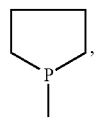

which may be substituted by $C_1$-$C_4$-alkyl or $C_1$-$C_4$-alkoxy in one or both ortho positions and, if appropriate, the metapositions relative to the P atom.

Examples of alkyl substituents on P, which preferably contain from 1 to 6 carbon atoms, are methyl, ethyl, n-propyl, i-propyl, n-butyl, i-butyl, t-butyl and the isomers of pentyl and hexyl. Examples of unsubstituted or alkyl-substituted cycloalkyl substituents on P are cyclopentyl, cyclohexyl, methylcyclohexyl and ethylcyclohexyl and dimethylcyclohexyl. Examples of alkyl-, alkoxy-, haloalkyl- and haloalkoxy-substituted phenyl or benzyl substituents on P are methylphenyl, dimethylphenyl, trimethylphenyl, ethylphenyl, methylbenzyl, methoxyphenyl, dimethoxyphenyl, trifluoromethylphenyl, bistrifluoromethylphenyl, tristrifluoromethylphenyl, trifluoromethoxyphenyl and bistrifluoromethoxyphenyl.

Preferred phosphino groups are ones which bear identical or different and preferably identical radicals selected from the group consisting of $C_1$-$C_6$-alkyl, unsubstituted cyclopentyl or cyclohexyl and cyclopentyl or cyclohexyl substituted by from 1 to 3 $C_1$-$C_4$-alkyl or $C_1$-$C_4$-alkoxy groups and benzyl and in particular phenyl which are unsubstituted or substituted by from 1 to 3 $C_1$-$C_4$-alkyl, $C_1$-$C_4$-alkoxy, F, Cl, $C_1$-$C_4$-fluoroalkyl or $C_1$-$C_4$-fluoroalkoxy groups.

The sec-phosphino group preferably corresponds to the formula —$PR_{14}R_{15}$, where $R_{14}$ and $R_{15}$ are each, independently of one another, a hydrocarbon radical which has from 1 to 20 carbon atoms and is unsubstituted or substituted by halogen, $C_1$-$C_6$-alkyl, $C_1$-$C_6$-haloalkyl, $C_1$-$C_6$-alkoxy, $C_1$-$C_6$-haloalkoxy, di-$C_1$-$C_4$-alkylamino, $(C_6H_5)_3Si$, $(C_1$-$C_{12}$-alkyl$)_3Si$ or —$CO_2$—$C_1$—$_6$-alkyl; or $R_{14}$ and $R_{15}$ together form unsubstituted or $C_1$-$C_4$-alkyl- or $C_1$-$C_4$-alkoxy-substituted dimethylene, trimethylene, tetramethylene or pentamethylene.

$R_{14}$ and $R_{15}$ are preferably identical or different and in particular identical radicals selected from the group consisting of branched $C_3$-$C_6$-alkyl, unsubstituted cyclopentyl or cyclohexyl and cyclopentyl or cyclohexyl substituted by from 1 to 3 $C_1$-$C_4$-alkyl or $C_1$-$C_4$-alkoxy groups, unsubstituted benzyl or benzyl substituted by from 1 to 3 $C_1$-$C_4$-alkyl or $C_1$-$C_4$-alkoxy groups and in particular unsubstituted phenyl or phenyl substituted by from 1 to 3 $C_1$-$C_4$-alkyl, $C_1$-$C_4$-alkoxy, —$NH_2$, OH, F, Cl, $C_1$-$C_4$-fluoroalkyl or $C_1$-$C_4$-fluoroalkoxy groups.

$R_{14}$ and $R_{15}$ are particularly preferably identical or different and in particular identical radicals selected from the group consisting of unsubstituted phenyl and phenyl substituted by from 1 to 3 $C_1$-$C_4$-alkyl, $C_1$-$C_4$-alkoxy and/or $C_1$-$C_4$-fluoroalkyl groups.

The process and intermediates of the invention are very well suited to the preparation of achiral and chiral aromatic ortho-diphosphines or other aromatic diphosphines which are suitable as chelating agents, which have been found to be valuable ligands in catalytically active metal complexes. The process is modular for the creation of different substitutions on the two P atoms and gives high yields. In addition, pure diastereomers or pairs of easily separated pairs of diastereomers can be prepared directly in a simple fashion and in high yields. The process is particularly useful for the preparation of such diphosphines on an industrial scale.

The invention further provides a process for preparing hydrocarbon-aromatic diphosphines having structural elements of the formula VI in an eyelopentadinyl ring,

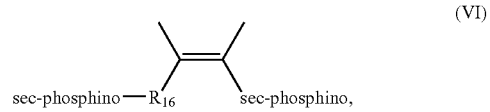

(VI)

or having structural elements of the formula VIa in each cyclopentadienyl ring of a ferrocene, bisindenylferrocene or ruthenocene,

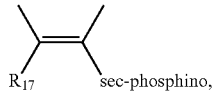

where
$R_{16}$ is a direct bond or a divalent bridging group, with the sec-phosphino in the bridging group being located in the 1,2 or 3 position relative to the carbon atom of the aromatic ring, and
$R_{17}$ is a substituent which is bound via a carbon atom to the cyclopentadienyl ring, which comprised the steps:
a) reaction of a ferrocene, bisindenylferrocene or ruthenocene having a structural element of the formula II

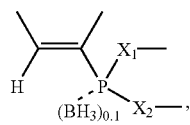

with metalation reagents to form a ferrocene, bisindenylferrocene or ruthenocene having a structural element of the formula I

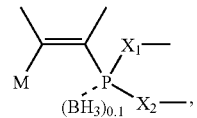

where M, $X_1$ and $X_2$ and hydrocarbon radicals bound to the free bonds of the groups $X_1$ and $X_2$ have the abovementioned meanings,
b) reaction of the compound of the formula I with an electrophilic and reactive compound, wherein
b1) the compound of the formula I is reacted with a sec-phosphine halide to introduce sec-phosphino,
b2) the compound of the formula I is reacted with an electrophilic reactive compound which has a reactive group which can be replaced by sec-phosphino in the 1,2 or 3 position and the product is subsequently reacted with a metal sec-phosphate or a secondary phosphine to introduce the group —$R_{16}$-sec—phosphino,
b3) the compound of the formula I is reacted with an electrophilic organic compound which forms an α-carbon atom to introduce the group -$R_{17}$,
c) any borane group present is removed from the compounds obtained in steps b1), b2) or
b3) and the radicals(hetero)hydrocarbon-$X_1$, (hetero)hydrocarbon-$X_2$ or $X_1$-(hetero)hydrocarbon-$X_2$ are subsequently split off to form a -$PCl_2$ group or -$PBr_2$ group and the Cl or Br atoms are then replaced by a hydrocarbon radical by means of an organometallic compound (Grignard reagent) to form the sec-phoshino group, or d)

the radicals (hetero)hydrocarbon-$X_2$ are split off to form a -$PCl_2$ group or -$PBr_2$ group and the Cl or Br atoms are then replaced by a hydrocarbon radical by means of an organometallic compound(Grignard) to form the sec-phosphino group and the borane group is then removed.

The individual process steps, advantages embodiments and preferences have been described above and are illustrated in the examples. Advantageous embodiments and preferences given for processes and compounds also apply to the above process.

A bridging group $R_{16}$ is preferably a radicals of the formulae

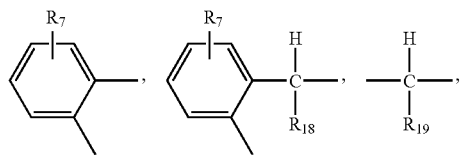

where
$R_7$ is as defined above,
$R_{18}$ is hydtroxyl, $C_1$-$C_4$-alkoxy, $C_1$-$C_1C_8$-acyloxy or sec-amino and
$R_{19}$ is $C_1$-$C_8$alkyl and preferably $C_1$-$C_4$-alkyl, unsubstituted or $C_1$-$C_4$-alkyl- or $C_1C_4$-alkoxy-substituted phenyl or benzyl.

$R_{17}$ is preferably a radical of the formula

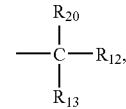

where
$R_{12}$ is hydrogen, $C_1$-$C_8$-alkyl and preferably $C_1$-$C_4$-alkyl, unsubstituted or $C_1$-$C_4$-alkyl- or $C_1$-$C_4$-alkoxy-substituted $C_4$-$C_8$-cycloalkyl or unsubstituted or $C_1$-$C_4$-alkyl- or $C_1$-$C_4$-alkoxy-substituted phenyl,
$R_{13}$ independently has one of the meanings of $R_{12}$ and
$R_{20}$ independently has one of the meanings of $R_{12}$ or is OH, $C_1$-$C_4$-alkoxy, $C_1$-$C_8$-acyloxy or sec-amino.

Examples of the individual meanings have been given above.

The process of the invention is, for example, particularly suitable for the economical preparation of Taniaphos ligands which have been found to be of interest especially in Ru-catalyzed enantioselective hydrogenations. The synthesis of amino-Taniaphos is described, for example, in WO 00/37478A1 and by T. Ireland et al. in Angew. Chem., 111 (1999), pages 3397-3400. These ligands can be prepared stereoselectively by the method according to the invention, since precursors can easily be separated into their optical isomers and the presence of chiral substituents effects optical inductions.

One preferred embodiment of the process of the invention is therefore a process for preparing 1-(α-substituted ortho-sec-phosphinobenzyl)-2-sec-phosphinoferrocenes of the formula VII in the form of their racemates, mixtures of diastereomers or essentially pure diastereomers,

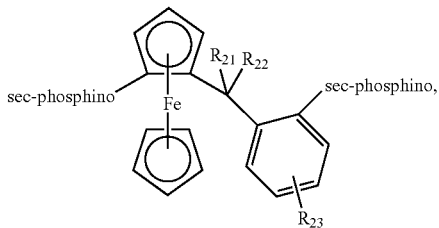

(VII)

where $R_{21}$ is hydrogen, $C_1$-$C_6$-alkyl, $C_3$-$C_8$-cycloalkyl, unsubstituted or F—, $C_1$-$C_6$-alkyl- or $C_1$-$C_6$-alkoxy-substituted phenyl or benzyl, $R_{22}$ is $C_1$-$C_4$-alkoxy, $C_1$-$C_8$-acyloxy or sec-amino and $R_{23}$ is hydrogen, $C_1$-$C_4$-alkyl or $C_1$-$C_4$-alkoxy, which comprises the steps:

a) reaction of a compound of the formula VIII

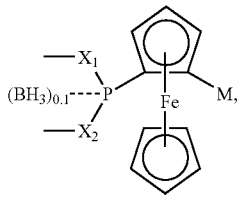

(VIII)

where

M and the group —P($X_1$—)($X_2$—) - - - $(BH_3)_{0,1}$ are as defined above, with a compound of the formula IX

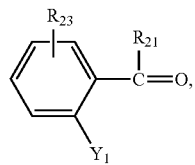

(IX)

where $Y_1$ is Cl, Br or I and $R_{23}$ is as defined above, to form a compound of the formula X,

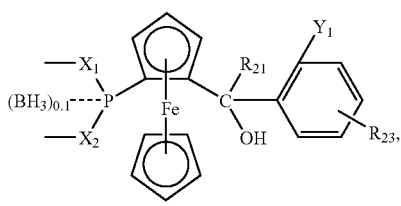

(X)

b) $C_1$-$C_4$-alkylation or $C_1$-$C_8$-acylation of the OH group in the compound of the formula X or replacement of the acyloxy group formed by sec-amino, c) replacement of the halogen $Y_1$ in compounds of the formula X by sec-phosphino and subsequent conversion of the group —P($X_1$—)($X_2$—) - - - $(BH_3)_{0,1}$, into a sec-phosphino group, or conversion of the group —P($X_1$—)($X_2$—) - - - $(BH_3)_{0,1}$ firstly into a sec-phosphino group and subsequent replacement of the halogen $Y_1$ in compounds of the formula X by sec-phosphino, d) preparation of the diphosphine of the formula VII, by d1) removing any borane group present from a compound of the formula X, then splitting off the radicals (hetero)hydrocarbon-$X_1$, (hetero)hydrocarbon-$X_2$ or $X_1$-(hetero)hydrocarbon-$X_2$ to form a —$PCl_2$ group or —$PBr_2$ group and then replacing the Cl or Br atoms by a hydrocarbon radical by means of an organometallic compound (Grignard reagent) to form the sec-phosphino group, or c2) splitting off the radicals (hetero)hydrocarbon-$X_1$, (hetero)hydrocarbon-$X_2$ or $X_1$-(hetero)hydrocarbon-$X_2$ to form a —$PCl_2$ group or —$PBr_2$ group and then replacing the Cl or Br atoms by a hydrocarbon radical by means of an organometallic compound (Grignard reagent) to form the sec-phosphino group and then removing the borane group.

The above-described advantageous embodiments and preferred embodiments apply to the radicals. The procedure for carrying out the process steps a) and d) has likewise been described above. Hydrocarbon radicals having at least one chiral carbon atom as have been described above are preferably bound to the group —P($X_1$—)($X_2$—) - - - $(BH_3)_{0,1}$ in order to achieve optical inductions for producing diastereomers or pairs of diastereomers.

The alkylation of process step b) can be carried out in a known manner, for example by formation of an —O-alkali metal group by means of an alkali metal hydride (potassium hydride) and subsequent reaction with an alkyl halide (methyl iodide). The acylation of process step b) is advantageously carried out using carboxylic anhydrides, preferably acetic anhydride. The reactions are preferably carried out in solution, with possible solvents having been mentioned above. The reaction temperatures can be in the range from −30° C. to 70° C.

The replacement of the acyloxy group in process step b) can be effected by means of secondary amines. Solvents used are preferably nitriles such as acetonitrile or carboxamides such as dimethylformamide. The reaction temperature can, for example, be from 20 to 120° C.

The replacement of the halogen $Y_1$ can be carried out by metalation of the halogen by means of, for example, a lithium alkyl (butyllithium) and subsequent reaction with a sec-phosphine halide, particularly preferably chlorides or bromides. The reactions are preferably carried out in solution, with possible solvents having been mentioned above. The reaction temperatures can be in the range from −100° C. to 30° C. The term sec-phosphine halide encompasses $H_2P$ halide, by means of which the —$PH_2$ group can be introduced, with this group subsequently being able to be converted as mentioned above into cyclic sec-phosphino groups.

The compounds of the formula VII are obtained in good total yields and, if desired, in high optical purities.

The invention also provides the intermediates obtained by the process of the invention in the form of racemates, diastereomers and pairs of diastereomers, in particular compounds of the formula XI,

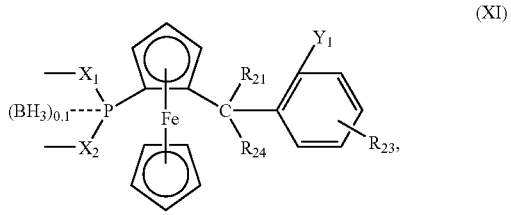

(XI)

where the group $-P(X_1-)(X_2-)$ - - - $(BH_3)_{0.1}$, $R_{21}$, $R_{22}$ and $Y_1$ are as defined above, or $(X_1-)$ and $(X_2-)$ in the group $-P(X_1-)(X_2-)$ - - - $(BH_3)_{0.1}$, are Cl or Br, and $R_{24}$ is $-OH$, $C_1$-$C_4$-alkoxy, $C_1$-$C_8$-acyloxy or sec-amino.

The process of the invention is described in more detail below. It has already been mentioned that the reaction of metalated metallocenes with prochiral electrophiles gives a mixture of diastereomers both with planar chirality and with chirality at the α-carbon. The use of suitable chiral groups $-P(X_1-)(X_2-)$ - - - $(BH_3)_{0.1}$ for example O-methylprolinol, leads to very high diastereoselectivity in respect of planar chirality and to a significant diastereoselectivity in respect of the chirality at the carbon. As a result, of the four possible diastereomers virtually only the diastereomers A and B

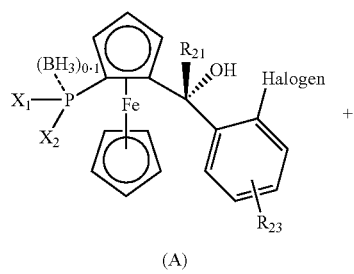

(A)

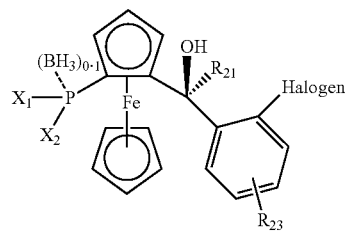

(B)

are formed and of these one is formed preferentially. If necessary, all diastereomers can be separated in a simple fashion thanks to the chiral group $-P(X_1-)(X_2-)$ - - - $(BH_3)_{0.1}$, in particular by chromatographic methods using chiral columns.

Each of the possible diastereomers can be converted into ligands of the formula VII. In the following, only the sequence starting from diastereomer A will be shown. For the preparation of ligands of the formula VII, the steps of the synthesis can be carried out in various orders.

In a first variant, the alcohol in compound A is deprotonated by means of a base (preferably KH) and converted by means of a monohalohydrocarbon R***-halogen into the corresponding ether of the formula C:

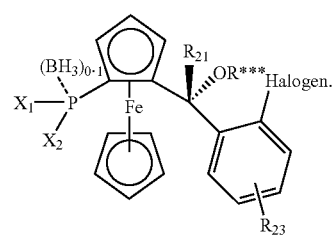

(C)

The reaction of compound (C) with a hydrohalic acid, preferably HCl, in a solvent (TBME, toluene) leads to the phosphine dihalide of the general formula D. If $X_1$ and/or $X_2$ are N, these are converted by addition of >2 equivalents of hydrohalic acid into the corresponding ammonium halides, which precipitate or are extracted in suitable solvents and can be recycled if required.

Phosphine compounds of the formula E are obtained by reacting the compounds D with organometallic reagents of the general formula $(R^o)_n$metal$^F$(halogen)$_{z-n}$, where z is the valence of the metal and n is equal to or less than z, particularly preferably with $R^o$—Li or $R^o$—Mg-halogen:

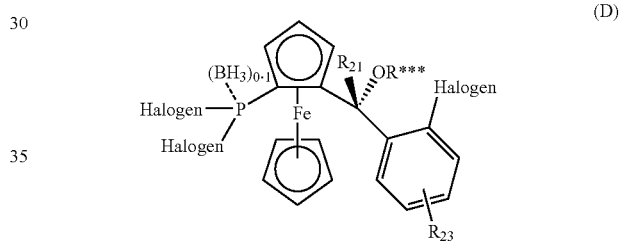

(D)

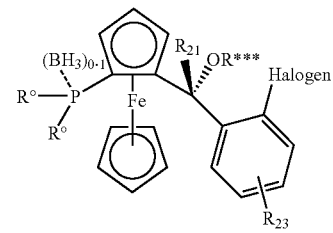

(E)

The compound E can be converted in a known manner by metalation of the C-halogen and subsequent reaction of the metalated compound with halogen-$P(R^{oo})_2$ into ligands of the formula VII having two identical or two different sec-phosphino radicals.

If a protective borane group is present, this can be removed by known methods at any stage (cf. M. Ohff et al., Synthesis (1998), page 1391. A preferred method is stirring of the compounds in the presence of, for example, diethylamine or DBU at temperatures of from 20° C. to 120° C.

If a borane group is present, this is preferably removed at the stage of the compound E or as last step to form ligands of the formula VII. Removal of the borane group from compound A can lead to the formation of cyclic products of the formula (F).

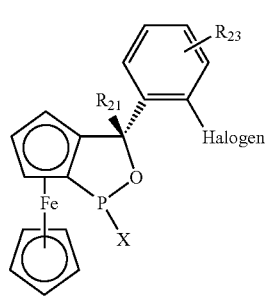
(F)

Compounds of the formula (F) can be converted by reaction firstly with a hydrohalic acid and subsequently with $(R°)_n\text{metal}^z(\text{halogen})_{z-n}$, preferably with $R°$—Li or $R°$—Mg-halide, into compounds of the general formula (H):

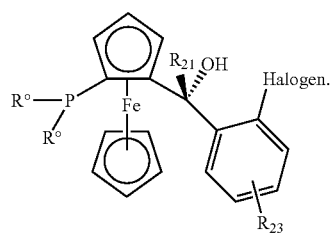
(H)

After deprotonation by means of a base (preferably KH) and reaction with a hydrocarbon-halide of the formula R***-halogen, the borane-free compound (J) is obtained:

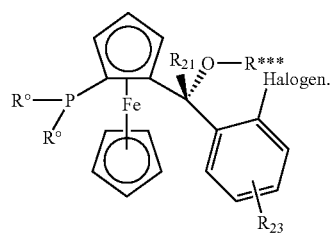
(J)

Compound D is converted by metalation of the C-halogen and subsequent reaction of the metalated species with halogen-P(R∞)₂ into compounds of the general formula (K):

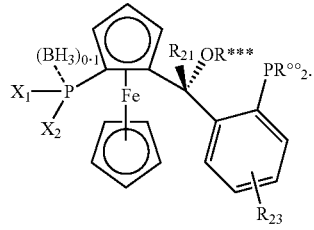
(K)

Reaction of the compound K with a hydrohalic acid gives the compound L which, as described above, can be converted by means of an R°-containing organometallic reagent into ligands of the formula VII:

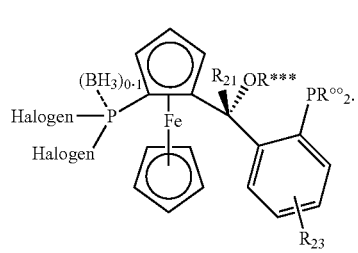
(L)

An alternative synthetic route proceeds via reaction of compound VIII with an aldehyde or ketone of the formula

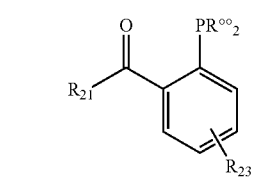

to form a compound M and M':

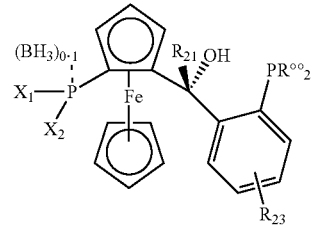
(M)

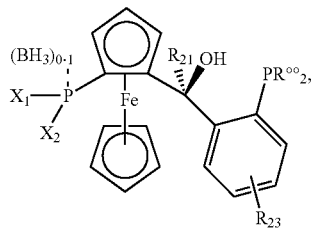
(M')

which, as described above, can be subjected to deprotonation of the alcohol and reaction with R***-halogen to give the compound K once again.

If a sec-amino group rather than the alkoxy group is to be bound to the chiral carbon atom, these compounds can be prepared in the following way. A compound A is converted, e.g. in acetic anhydride, into the acetate of the general formula (N):

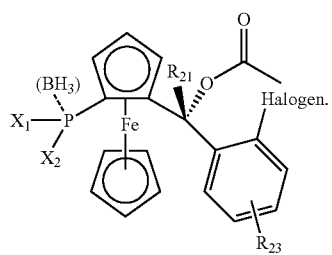

(N)

After reaction with HN(R***)$_2$, the amine of the general formula (O) is obtained:

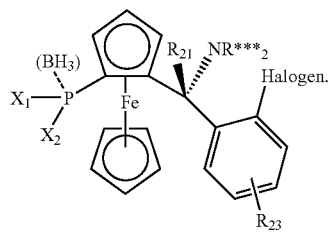

(O)

It is also possible firstly to convert the compound of the formula (M) into the acetate compound of the formula (P) by means of acetic anhydride and subsequently react the compound of the formula (P) with HN(R***)$_2$ to give the amine compound of the formula (Q):

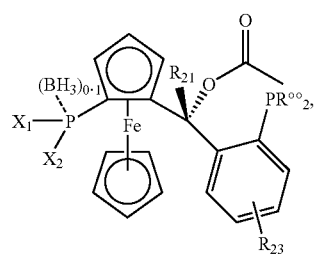

(P)

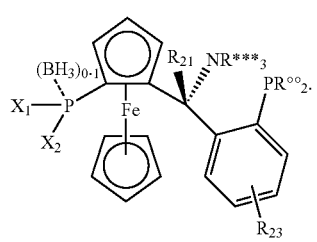

(Q)

A further possibility is reaction of compounds of the formula H with acetic anhydride to form compounds of the formula (R)

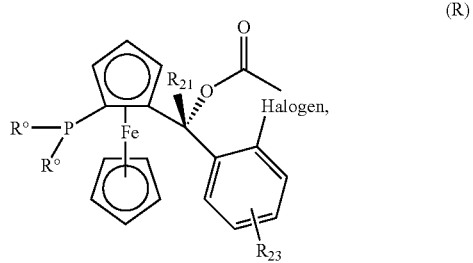

(R)

and subsequently with HN(R***)$_2$ to give compounds of the formula (T).

The amine compounds of the formulae (O) and (Q) can be converted in a manner analogous to the ether compounds of the formula C into ligands of the formula VII. In this case, the synthesis occurs via the following intermediates S, T, U and W:

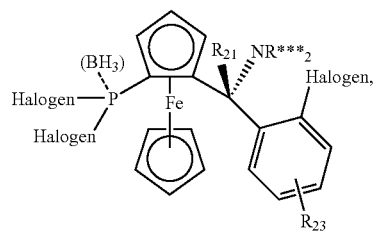

(S)

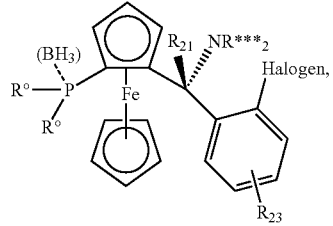

(T)

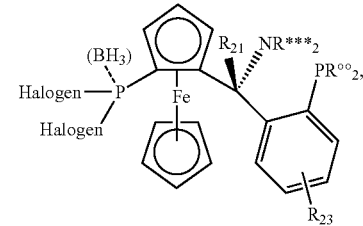

(U)

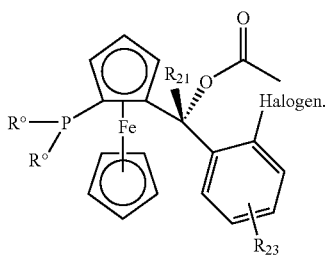

(W)

Diphosphine ligands which have identical or different deephosphino groups bound directly to ferrocenes, bisindenylferrocenes or ruthenocene, in the 1, 2 positions can be prepared in a particularly economical way in few process steps by means of the process of the invention. Another preferred embodiment of the process of the invention is a process for preparing compounds of the formula XII in the form of racemates, diastereomers and pairs of diastereomers,

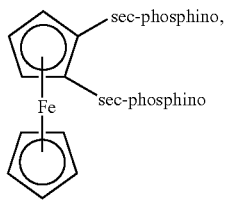
(XII)

which comprises the steps a) reaction of a compound of the formula XIV

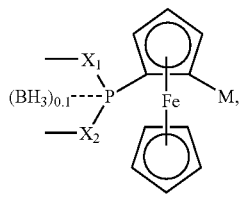
(XIV)

where

M, and the group -P($X_1$-)----$(BH_3)_{0.1}$ are defined above, with a sec-phosphine halide(chloride or bromide) to produce compounds of the formula XVI,

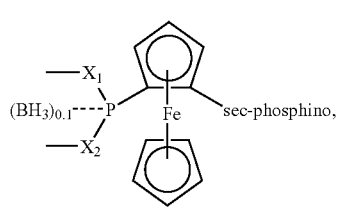
(XVI)

b) preparation of diphosphines of the formulae XII by b1) removing any borane group present from a compound if the formula XVI or, then splitting off the radicals(hetero)hydrocarbon-$X_1$,(hetero)hydrocarbon-$X_2$ or $X_1$-(hetero)hydrocarbon-$X_2$ $_{to\ form\ a\ -PCl2}$ group or _$PBr_2$ group and then replacing the Cl or Br atoms by a hydrocarbon radical by means of an organometallic compound (Grignard reagent) to form the sec-phosphino group, or b2) splitting off the radicals (hetero)hydrocarbon-$X_1$,(hetero)hydrocarbon-$X_2$ or $X_1$-(hetero)hydrocarbon-$X_2$ to form a -$PCl_2$ group and then replacing the Cl or Br atoms by a hydrocarbon radical by means of an organometallic compound (Grignard reagent) to form the sec-phosphino group and then removing the borane group.

The above-described advantageous embodiments and preferred embodiments apply to the radicals. The procedure for carrying out the process steps a) and b) has likewise been described above. In the case of ferrocenes, hydrocarbon radicals having at least one chiral carbon atom, as have been described above, are preferably bound to the group —P($X_1$—)($X_2$—) - - - $(BH_3)_{0.1}$ in order to achieve optical inductions for preparing diastereomers of planar-chiral ferrocenes.

The invention also provides the novel intermediates which occur in this process in the form of racemates, diastereomers and pairs of diastereomers, in particular those of the formulae XVI and XVIII,

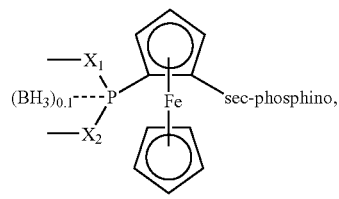
(XVI)

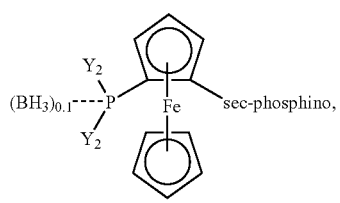
(XVIII)

where the group —P($X_1$—)($X_2$—) - - - $(BH_3)_{0.1}$ is as defined above and $Y_2$ is Cl or Br.

The process of the invention is also particularly useful for preparing bisferrocenyldiphosphine ligands, especially those having different sec-phosphino groups. A further preferred embodiment of the process of the invention is a process for preparing compounds of the formula XIX in the form of racemates, diastereomers and pairs of diastereomers,

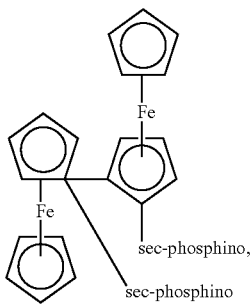
(XIX)

where sec-phosphino is as defined above, which comprises the steps a) reaction of a compound of the formula XX with a compound of the formula XXI,

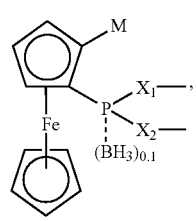
(XX)

-continued (XXI)

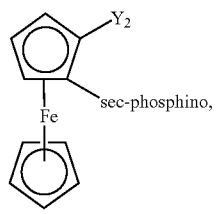

where

M is —Sn(C$_1$-C$_4$-alkyl)$_3$ or —ZnX$_3$, the group —P(X$_1$—)(X$_2$—) - - - (BH$_3$)$_{0.1}$ is as defined above and Y$_2$ is I or Br, in the presence of a Pd catalyst to form a compound of the formula XXII (XXII)

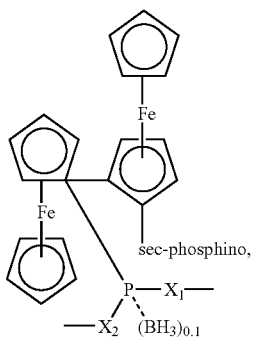

b) preparation of diphosphines of the formula XIX by b1) removing any borane group present from a compound of the formula XXII, then splitting off the radicals (hetero)hydrocarbon-X$_1$, (hetero)hydrocarbon-X$_2$ or X$_1$-(hetero)hydrocarbon-X$_2$ to form a —PCl$_2$ group or —PBr$_2$ group and then replacing the Cl or Br atoms by a hydrocarbon radical by means of an organometallic compound (Grignard reagent) to form the sec-phosphino group, or b2) splitting off the radicals (hetero)hydrocarbon-X$_1$, (hetero)hydrocarbon-X$_2$ or X$_1$-(hetero)hydrocarbon-X$_2$ to form a —PCl$_2$ group or —PBr$_2$ group and then replacing the Cl or Br atoms by a hydrocarbon radical by means of an organometallic compound (Grignard reagent) to form the sec-phosphino group and then removing the borane group.

The above-described advantageous embodiments and preferred embodiments apply to the radicals. The procedure for carrying out the process steps a) and b) has likewise been described above. Hydrocarbon radicals having at least one chiral carbon atom, as have been described above, are preferably bound to the group —P(X$_1$—)(X$_2$—) - - - (BH$_3$)$_{0.1}$ in order to achieve optical inductions for preparing diastereomers of planar-chiral ferrocenes. A suitable Pd catalyst is, for example, Pd(dba)$_3$.

The invention also provides the novel intermediates occurring in this process in the form of racemates, diastereomers and pairs of diastereomers, in particular those of the formulae XXII and XXIII, (XXII)

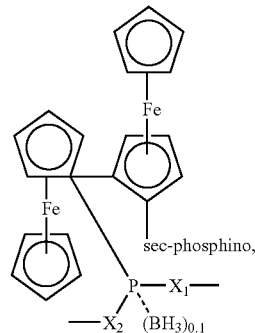

(XXIII)

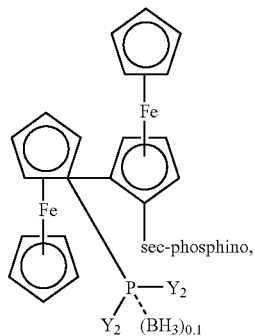

where the group —P(X$_1$—)(X$_2$—) - - - (BH$_3$)$_{0.1}$ is as defined above and Y$_2$ is Cl or Br.

The process of the invention is also particularly useful for preparing ferrocenyldisphosphine ligands, in particular those having different sec-phosphino groups, in which a phosphino group is bound via a chiral carbon atom to a cyclopentadienyl ring. A further preferred embodiment of the process of the invention is a process for preparing compounds of the formula XXIV in the form of racemates, diastereomers and pairs of diastereomers, (XXIV)

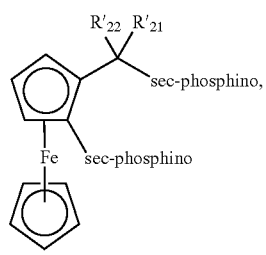

where

R'$_{21}$ is hydrogen,

R'$_{22}$ is C$_1$-C$_6$-alkyl, C$_3$-C$_8$-cycloalkyl, unsubstituted or F—, C$_1$-C$_6$-alkyl- or C$_1$-C$_6$-alkoxy-substituted phenyl or benzyl, which comprises the steps a) reaction of a compound of the formula XX, (XX)

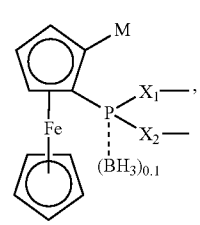

with an aldehyde or ketone of the formula $R_{21}R_{22}C(O)$ to form a compound of the formula XXV,

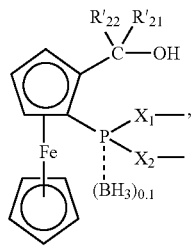
(XXV)

b) preparation of compounds of the formula XXVI,

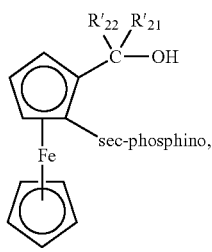
(XXVI)

by b1) removing any borane group present from a compound of the formula XXV, then splitting off the radicals (hetero)hydrocarbon-$X_1$, (hetero)hydrocarbon-$X_2$ or $X_1$-(hetero)hydrocarbon-$X_2$ to form a —$PCl_2$ group or —$PBr_2$ group and then replacing the Cl or Br atoms by a hydrocarbon radical by means of an organometallic compound (Grignard reagent) to form the sec-phosphino group, or b2) splitting off the radicals (hetero)hydrocarbon-$X_1$, (hetero)hydrocarbon-$X_2$ or $X_1$-(hetero)hydrocarbon-$X_2$ to form a —$PCl_2$ group or —$PBr_2$ group and then replacing the Cl or Br atoms by a hydrocarbon radical by means of an organometallic compound (Grignard reagent) to form the sec-phosphino group and then removing the borane group, c) acylating the compound of the formula XXVI, for example by means of a carboxylic anhydride, and d) replacing the $C_1$-$C_8$-acyloxy group formed by means of a secondary phosphine to give compounds of the formula XXIV.

The above-described advantageous embodiments and preferred embodiments apply to the radicals. The procedure for carrying out the process steps a) and b) has likewise been described above. In the case of ferrocenes, hydrocarbon radicals having at least one chiral carbon atom, as have been described above, are preferably bound to the group —$P(X_1—)(X_2—)$ - - - $(BH_3)_{0.1}$ in order to achieve optical inductions for preparing diastereomers of planar-chiral ferrocenes. Process steps c) and d) are known reactions.

The reaction sequence can, for example, be illustrated by the following reaction scheme:

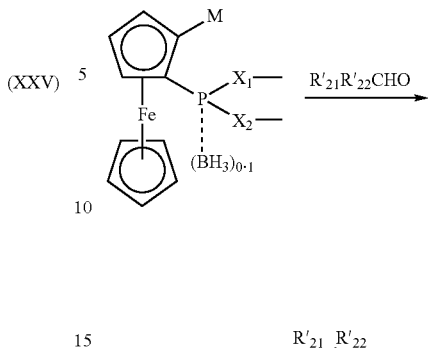

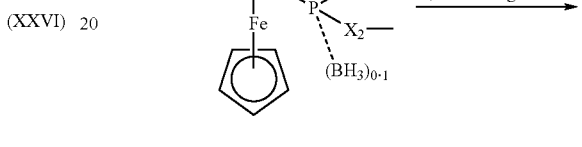

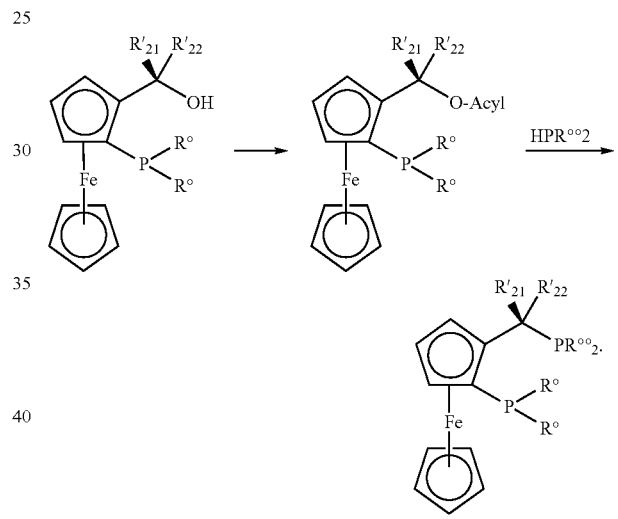

The invention also provides the novel intermediates occurring in this process in the form of racemates, diastereomers and pairs of diastereomers, in particular those of the formulae XXVII and XXVIII, (XXVII)

(XXVIII)

where $R_{21}$, $R_{22}$, $Y_2$ and the group —$P(X_1—)(X_2—)$ - - - $(BH_3)_{0.1}$ are as defined above.

The process of the invention is also particularly useful for preparing Ferrocenyldiphosphine ligands, in particular those having different sec-phosphino groups, In which a phosphino group is present in the ortho position of a phenyl substituent of the Cyclopentadienyl ring. A further preferred embodiment of the process of the invention is a process for preparing compounds of the formula XXIX in the form of racemates, diastereomers and pairs of diastereomers,

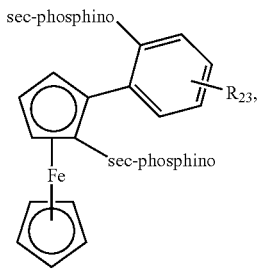
(XXIX)

which comprises the steps
a) reaction of a compound of the formula XX

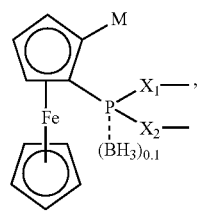
(XX)

where M is prederably —Sn($C_1$—$C_4$-alkyl)$_3$ or —ZnX$_3$, the group —P($X_1$—)($X_2$—)---($BH_3$)$_{0.1}$ is as defined above, with 1-bromo-2-iodobenzene or 1,2-diiodobenzene in the presence of a Pd catalyst to form a compound of the formula XXX,

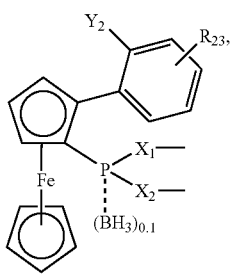
(XXX)

where $Y_2$ is bromine or iodine,
b) to prepare monophosphines of the formula XXXI

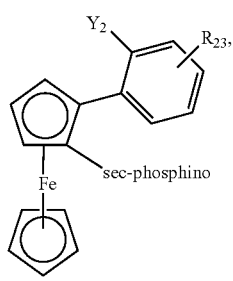
(XXXI)

b1) removing any borane group present from a compound of the formula XXX, then splitting off the radicals (hetero)hydrocarbon-$X_1$, (hetero)hydrocarbon-$X_2$ or $X_1$-(hetero)-hydrocarbon-$X_2$ to form a —$PCl_2$ group or —$PBr_2$ group and then replacing the Cl or Br atoms by a hydrocarbon radical by means of an organometallic compound (Grignard reagent) to form the sec-phosphino group, or b2) splitting off the radicals (hetero)hydrocarbon-$X_1$, (hetero)hydrocarbon-$X_2$ or $X_1$-(hetero)hydrocarbon-$X_2$ to form a —$Pd_2$ group or —$PBr_2$ group and then replacing the Cl or Br atoms by a hydrocarbon radical by means of an organometallic compound (Grignard reagent) to form the sec-phosphino group and then removing the borane group, and c) then replacing the bromine or iodine atom by a sec-phosphino group by metalation by means of a lithium alkyl (butyllithium) and subsequent reaction with a sec-phosphine halide, or d) to prepare compounds of the formula XXXII

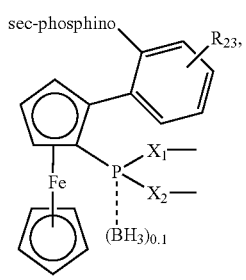
(XXXII)

reacting a compound of the formula XX with ortho-sec-phosphinophenyl iodide in the presence of metal halides such as $ZnBr_2$ and Pd catalysts, and d1) removing any borane group present from a compound of the formula XXXII, then splitting off the radicals (hetero)hydrocarbon-$X_1$, (hetero)hydrocarbon-$X_2$ or $X_1$-(hetero)-hydrocarbon-$X_2$ to form a —$PCl_2$ group or —$PBr_2$ group and then replacing the Cl or Br atoms by a hydrocarbon radical by means of an organometallic compound (Grignard reagent) to form the sec-phosphino group, or d2) splitting off the radicals (hetero)hydrocarbon-$X_1$, (hetero)hydrocarbon-$X_2$ or $X_1$-(hetero)hydrocarbon-$X_2$ to form a —$PCl_2$ group or —$PBr_2$ group and then replacing the Cl or Br atoms by a hydrocarbon radical by means of an organometallic compound (Grignard reagent) to form the sec-phosphino group and then removing the borane group.

The above-described advantageous embodiments and preferred embodeiments apply to the radicals. The procedure for carrying out the individual process steps has likewise been described above. Hydrocarbon radicals having at least one chiral carbon atom, as have been described above, are preferably bound to the group —P($X_1$—)($X_2$—)---($BH_3$)$_{0.1}$ in order to achieve optical inductions for preparing diastereomers of planar-chiral ferrocenes. Process steps c) and d) are known reactions The reaction sequence can be illustrated, for example, by the following reaction scheme:

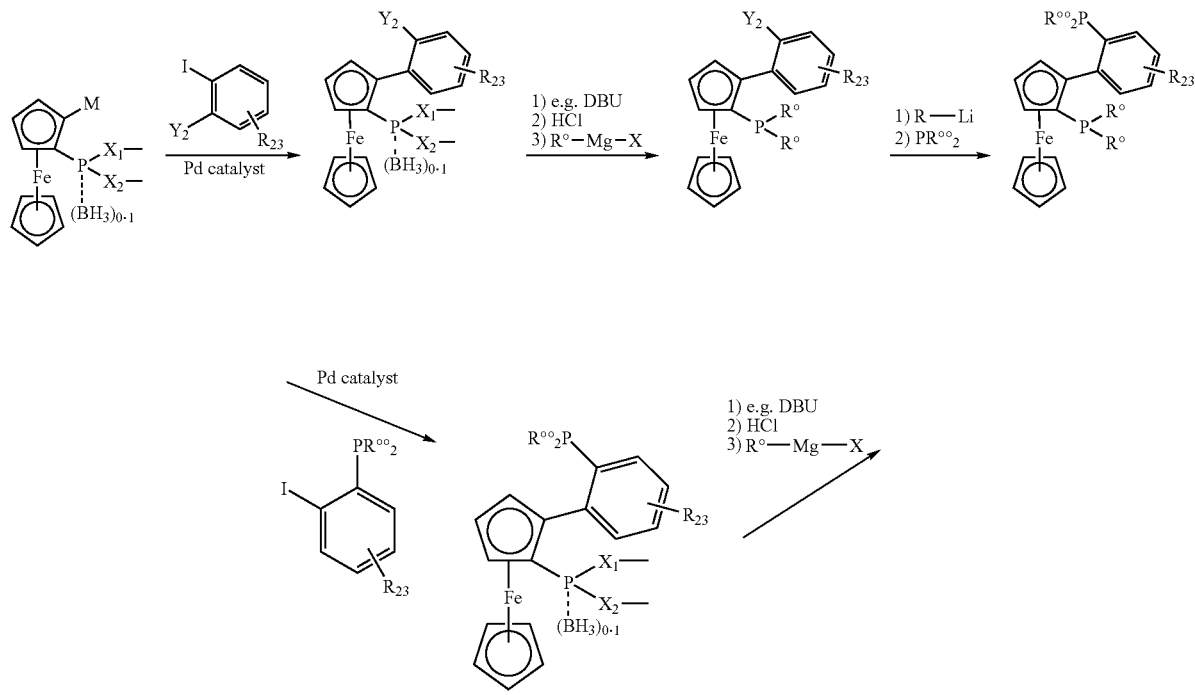

The invention also provides the novel intermediates occurring in this process in the form of racemates, diastereomers and pairs of diastereomers, in particular those of the formulae XXX, XXXII, XXXIII and XXXIV,

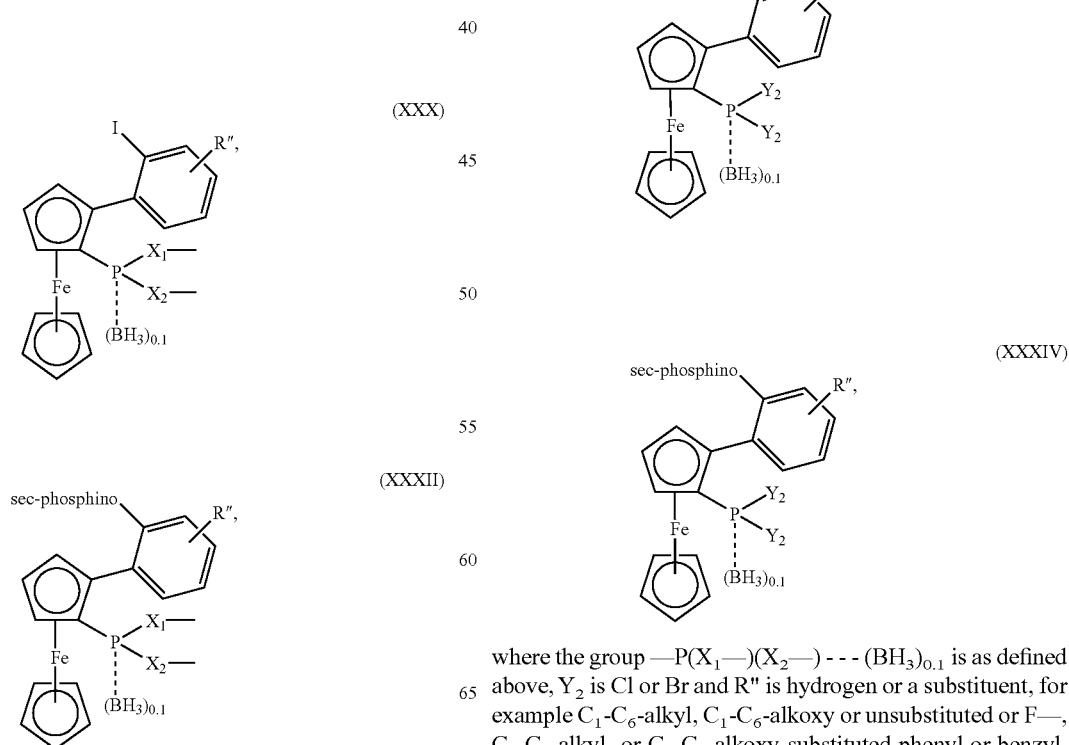

where the group —P($X_1$—)($X_2$—) - - - $(BH_3)_{0.1}$ is as defined above, $Y_2$ is Cl or Br and R" is hydrogen or a substituent, for example $C_1$-$C_6$-alkyl, $C_1$-$C_6$-alkoxy or unsubstituted or F—, $C_1$-$C_6$-alkyl- or $C_1$-$C_6$-alkoxy-substituted phenyl or benzyl.

The process of the invention is also particularly useful for preparing ferrocenyldiphosphine ligands in which a phosphine group is bound to each cyclopentadienyl ring and a substituted hydrocarbon radical which may have a chiral a-carbon atom is present in the ortho position relative thereto. A further preferred embodiment of the process of the invention is a process for preparing compounds of the formula XXXV in the form of racemates, diastereomers and pairs of diastereomers,

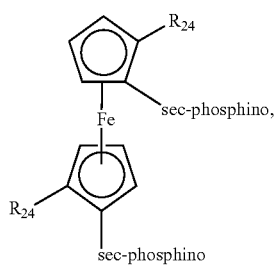

(XXXV)

where $R_{24}$ is a radical of the formula —$CR_{25}R_{26}$—$Y_3$ or a group $R_{28}$, $R_{25}$ is hydrogen, $C_1$-$C_6$-alkyl, $C_3$-$C_8$-cycloalkyl, unsubstituted or F—, $C_1$-$C_6$-alkyl- or $C_1$-$C_6$-alkoxy-substituted phenyl or benzyl, $R_{26}$ is $C_1$-$C_6$-alkyl, $C_3$-$C_8$-cycloalkyl, unsubstituted or F-, $C_1$-$C_6$-alkyl- or $C_1$-$C_6$-alkoxy-substituted phenyl or benzyl, $Y_3$ is $C_1$-$C_4$-alkoxy, $C_1$-$C_8$-acyloxy or sec-amino and $R_{28}$ is $C_1$-$C_6$-alkyl, $C_3$-$C_8$-cycloalkyl, unsubstituted or F-, $C_1$-$C_6$-alkyl- or $C_1$-$C_6$-alkoxy-substituted phenyl or benzyl, which comprises the steps a) reaction of a compound of the formula XXXVI

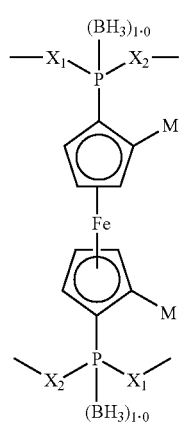

(XXXVI)

where the group —$P(X_1$—$)(X_2$—$)$ - - - $(BH_3)_{0.1}$ is as defined above, with an aldehyde or ketone or imine of the formula $CR_{25}R_{26}$=$Y_4$, where $Y_4$ is =O or =N($C_1$-$C_4$-alkyl), or with a halide $R_{28}Y_6$, where $Y_6$ is Cl, Br or iodine, to form compounds of the formula XXXVII

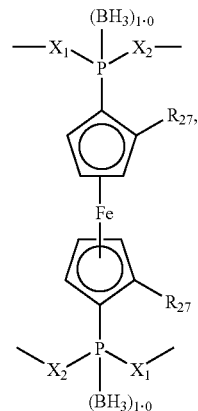

(XXXVII)

where $R_{27}$ is the group —$CR_{25}R_{26}$—$Y_5$ or $R_{28}$, where $R_{25}$ and $R_{26}$ are as defined above and $Y_5$ is —OH or —NH($C_1$-$C_4$-alkyl), alkylating the NH group, if appropriate alkylating or acylating the OH group and, if appropriate, replacing the acyloxy group by sec-amino and b) to prepare compounds of the formula XXXV b1) removing any borane group present from a compound of the formula XXXVII, then splitting off the radicals (hetero)hydrocarbon-$X_1$, (hetero)hydrocarbon-$X_2$ or $X_1$-(hetero)-hydrocarbon-$X_2$ to form a —$PCl_2$ group or —$PBr_2$ group and then replacing the Cl or Br atoms by a hydrocarbon radical by means of an organometallic compound (Grignard reagent) to form the sec-phosphino group, or b2) splitting off the radicals (hetero)hydrocarbon-$X_1$, (hetero)hydrocarbon-$X_2$ or $X_1$-(hetero)hydrocarbon-$X_2$ to form a —$PCl_2$ group or —$PBr_2$ group and then replacing the Cl or Br atoms by a hydrocarbon radical by means of an organometallic compound (Grignard reagent) to form the sec-phosphino group and then removing the borane group.

The advantageous embodiments and preferred embodiments described above apply to the radicals. The procedure for carrying out the individual process steps has likewise been described above. Hydrocarbon radicals having at least one chiral carbon atom, as have been described above, are preferably bound to the group —$P(X_1$—$)(X_2$—$)$ - - - $(BH_3)_{0.1}$ in order to achieve optical inductions for preparing diastereomers of planar-chiral and C-chiral ferrocenes. The modifications of process step a) in respect of alkylation, acylation and amine substitution are known reactions.

The invention also provides the novel intermediates occurring in this process in the form of racemates, diastereomers and pairs of diastereomers, in particular those of the formulae XXXVII and XXXVIII,

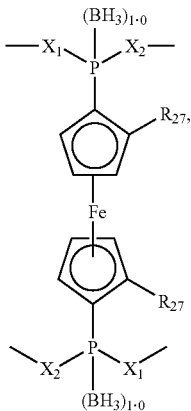

(XXXVII)

(XXXVIII)

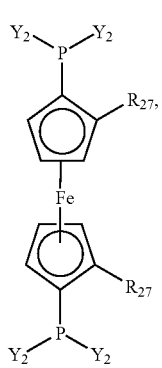

where
$R_{27}$ and $Y_2$ are as defined above.

1,2-Di(PH$_2$)benzene or 1-sec-phosphino-2-PH$_2$-benzene can also be prepared in a simple manner by means of the process of the invention, by a) reacting compounds of the formula XV with di(sec-amino) phosphine monohalides (chlorides, bromides) to introduce di(sec-amino)phosphino groups such as di(dimethylamino)phosphino, di(diethylamino)phosphino, N,N-diethylcyclohexylenediaminophosphino; phosphoric ester monohalides (chlorides, bromides) to introduce phosphonic ester groups such as (CH$_3$O)$_2$(O)P—, (C$_2$H$_5$O)(O)P—, (cyclohexylO)$_2$(O)P—, (ethylenedioxyl)(O)P—;

phosphorous ester monohalides (chlorides, bromides) to introduce phosphorous ester groups such as (CH$_3$O)$_2$P—, (C$_2$H$_5$O)$_2$P—, (cyclohexylO)$_2$P—, (ethylenedioxyl)P—;

or with a secondary phosphine halide, b1) removing any borane group present in the compounds obtained, then splitting off the (hetero)hydrocarbon-X$_1$, (hetero)hydrocarbon-X$_2$ or X$_1$-(hetero)hydrocarbon-X$_2$ to form a —PCl$_2$ group or —Br$_2$ group and then hydrogenating the —PCl$_2$ group or —PBr$_2$ group to form a PH$_2$ group (for example by means of Li(AlH$_4$), or b2) splitting off the radicals (hetero)hydrocarbon-X$_1$, (hetero)hydrocarbon-X$_2$ or X$_1$-(hetero)hydrocarbon-X$_2$ to form a —PCl$_2$ group or —PBr$_2$ group and then hydrogenating the —PCl$_2$ group or —PBr$_2$ group to form a PH$_2$ group and then removing the borane group. 1,2-Di(PH$_2$) benzene and 1-sec-phosphino-2-PH$_2$-benzene are valuable intermediates for preparing benzene-1,2-diphosphetanes as chiral ligands for metal complexes for the enantioselective catalytic hydrogenation of prochiral compounds.

The processes of the invention allow an efficient and economical preparation of aromatic phosphine ligands which can be carried out on an industrial scale and provide a wide variety of possibilities for preparing different monophosphines and diphosphines.

The following examples illustrate the invention.

A) Preparation of Halophosphines

EXAMPLE A1

Preparation of

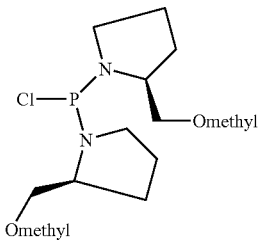

In a 500 ml round-bottom flask provided with an argon inlet, PCl$_3$ (7.38 g, 53.75 mmol) is dissolved in dry tetrahydrofuran (THF, 150 ml) under argon and the solution is cooled to 0° C. in an ice bath. Triethylamine (11.97 g, 118.25 mmol, 2.20 equivalents) is added dropwise and (S)methoxymethylpyrrolidine (12.69 g, 110.19 mmol, 2.05 equivalents) is then slowly added dropwise. During the addition, the formation of a white precipitate is observed. The ice bath is removed and the suspension obtained is stirred overnight (14 h) at room temperature (RT). The white precipitate formed is filtered off under argon by means of a double-ended frit filter and washed with dry THF (2×25 ml). A $^{31}$P-NMR spectrum (C$_6$D$_6$) of the yellowish filtrate obtained is recorded. The solution obtained in this way is reacted without further purification. $^{31}$P-NMR (C$_6$D$_6$, 121 MHz): 154.3 (s).

EXAMPLE A2

Preparation of

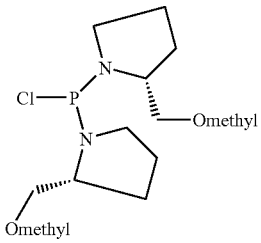

The procedure of example A1 is repeated using (R)methoxymethylpyrrolidine.

EXAMPLE A3

Preparation of

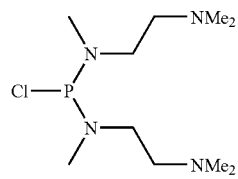

8.6 ml (11.2 mmol) of a 1.3M s-butyllithium solution in cyclohexane/hexane (98:2) are added dropwise to a solution of 1.48 ml (11.4 mmol) of N,N',N'-trimethylethylenediamine in 70 ml of THF at −78° C. The mixture is subsequently stirred at −20° C. for 20 minutes. After cooling back down to −78° C., a solution of 0.47 ml (5.4 mmol) of PCl$_3$ in 140 ml of THF is added dropwise and the mixture is allowed to warm to RT overnight while stirring. Distilling off the solvent under a high vacuum gives the title compound as an oily substance which can be used further without further purification.

EXAMPLE A4

Preparation of

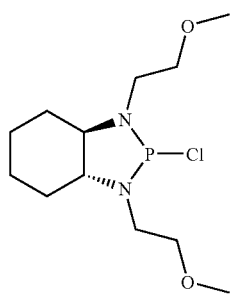

15.4 ml (38.5 mmol) of a 2.5 molar n-butyllithium solution in hexane are added dropwise to 4.20 g (18.2 mmol) of (R,R-N,N'-bis(methoxyethyl)cyclohexane-1,2-diamine in 300 ml of THF at −78° C. The mixture is subsequently stirred at −20° C. for 20 minutes, then cooled back down to −78° C. and 3.60 ml (41.3 mmol) of PCl$_3$ are added. The mixture is allowed to warm to RT overnight while stirring. Distilling off the solvent and the excess PCl$_3$ under reduced pressure gives the compound A4 as a viscous oil which is used further without further purification. $^{31}$P-NMR (C$_6$D$_6$, 162 MHz): 173.7 (s).

B) Preparation of Aromatic Monophosphines and Diphosphines

EXAMPLE B1

Preparation of

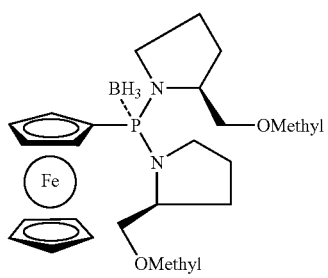

In a 1 l round-bottom flask provided with an argon inlet, ferrocene (10.00 g, 53.75 mmol) and potassium tert-butoxide (754 mg, 6.72 mmol, 0.125 equivalent) are dissolved in dry THF (100 ml) under argon. The solution is cooled to −78° C. and t-butyllithium (1.5 M in hexane; 71.67 ml, 107.50 mmol, 2.00 equivalents) is added dropwise over a period of 45 minutes. The solution is stirred at −78° C. for 1.5 hours and admixed with n-heptane (75 ml). After the precipitate obtained has settled, the supernatant solution is removed by means of a hollow needle under argon pressure at −78° C. The precipitate is washed with n-heptane (60 ml) at −78° C. and the washings are removed again by means of a hollow needle. This procedure is repeated three times. The precipitate obtained is dissolved in dry THF (50 ml) and a solution of A1 (53.75 mmol, 1.00 equivalent) in THF (200 ml) is added dropwise over a period of 1.5 hours at −78° C. The solution is stirred overnight (14 h) while warming to RT. Borane-dimethyl sulfide complex (5.10 ml, 53.75 mmol, 1.00 equivalent) is subsequently added dropwise and the mixture is stirred overnight at RT. The reaction mixture is hydrolyzed with saturated NH$_4$Cl solution (50 ml) and extracted with tert-butyl methyl ether (TBME) (3×100 ml). The combined organic phases are dried over Na$_2$SO$_4$ and the solvent is distilled off on a rotary evaporator. The crude product (24.18 g) is purified by column chromatography (200 g of silica gel, n-heptane/TBME 5:1). The title compound (17.23 g, 70% of theory) is obtained as an orange solid. $^3$P-NMR (C$_6$D$_6$, 121 MHz): 80.8 (m, broad).

EXAMPLE B2

Preparation of

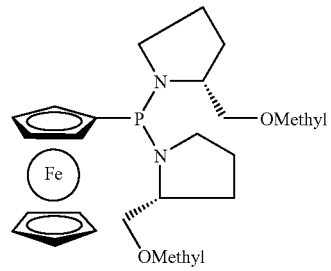

17.9 mmol of a 1.6 molar n-butyllithium solution in hexane are slowly added dropwise to a solution of 4.53 g (17.1 mmol) of bromoferrocene in 15 ml of THF at −78° C. and the mixture is stirred at this temperature for 10 minutes. The temperature is then allowed to rise to 0-5° C. (ice cooling), a solution of 18.8 mmol of the compound from example A2 in 78 ml of THF is added dropwise and the mixture is stirred overnight at RT. The solvent is subsequently taken off and the crude product is purified on a short column (silica gel 60 from Fluka, eluent: TBME). Distillation of the colored fractions on a rotary evaporator gives an orange, almost solid, oil. $^{31}$P-NMR (C$_6$D$_6$, 121 MHz): 70.7 (s).

EXAMPLE B3

Preparation of

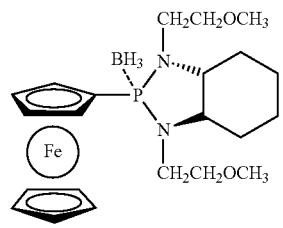

a) Synthesis of

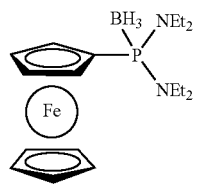

In a 0.5 l round-bottom flask provided with an argon inlet, ferrocene (4.00 g, 21.5 mmol) and potassium tert-butoxide (305 mg, 27 mmol, 0.125 equivalent) are dissolved in dry THF (100 ml) under argon. The solution is cooled to −78° C. and t-butyllithium (1.5 M in hexane; 29 ml, 43 mmol, 2.00 equivalents) is added dropwise over a period of 45 minutes. The solution is stirred at −78° C. for 1.5 hours and ferrocenyllithium is precipitated by addition of n-pentane (75 ml). After the precipitate obtained has settled, the supernatant solution is removed by means of a hollow needle under argon pressure at −78° C. After replacement of the solvent by pentane, a solution of bis(diethylamino)chlorophosphine (4.04 g, 19.3 mmol) in 30 ml of absolute ether is added and the mixture is allowed to warm to room temperature overnight. The dark orange solution is decanted off, evaporated in a high vacuum, dissolved in 50 ml of absolute toluene and admixed at 0° C. with borane-dimethyl sulfide (10 M, 2.32 ml, 23.2 mmol). After one hour at room temperature, the solvent is distilled off under reduced pressure and the product is obtained as an orange solid (6.87 g, 95%) after recrystallization from pentane. $^{31}$P-NMR (C$_6$D$_6$, 162 MHz): δ=90.2 (q, J=83 Hz).

b) The compound prepared as described in a) (374 mg, 1.0 mmol) together with degassed morpholine (5.0 ml) are heated overnight at 100° C. under argon, subsequently evaporated in a high vacuum, taken up in absolute ether and, at 0° C., HCl in ether (2.0 M, 5 ml, 10 mmol) is added dropwise. After two hours at room temperature, the mixture is filtered under argon and the solvent volume is reduced to about 5 ml. At 0° C., a solution of ethyl$_3$N in absolute diethyl ether and (R,R)-N,N'-bismethoxyethylcyclohexane-1,2-diamine (205 mg, 0.9 mmol) is added (preparation of the diamine as described by A. Alexakis, A. S. Chauvin, R. Stouvenel, E. Vrancken, S. Mutti, P. Mangeney Tetrahedron: Asymmetry 2001, 12, 1171). The reaction mixture is stirred overnight at RT, then filtered and, after evaporation with toluene (6 ml) admixed at 0° C. with borane-dimethyl sulfide (10.0 M, 0.12 ml, 1.2 mmol). Purification on an Alox column using hexane:ethyl acetate (5:1) gives 250 mg (0.55 mmol, 61%) of an orange solid (55%).

$^1$H-NMR (C$_6$D$_6$, 400 MHz): δ=4.62-4.58 (m, 1H); 4.24 (s, 5H, Cp-H); 4.20-4.17 (m, 1H); 4.17-4.12 (m, 1H); 4.10-4.07 (m, 1H); 3.80-3.67 (m, 2H); 3.60-3.54 (m, 1H); 3.48-3.27 (m, 3H); 3.22-3.09 (m, 1H); 3.15 (s, 3H); 3.07 (s, 3H); 2.78-2.61 (m, 2H); 2.40-2.32 (m, 1H); 2.15-1.20 (m, 3H); 2.10-2.02 (m, 1H); 1.80-1.72 (m, 1H); 1.54-1.40 (m, 2H); 1.08-0.84 (m, 4H).

$^{31}$P-NMR (C$_6$D$_6$, 162 MHz): δ=104.5 (q, J$_{PB}$=87 Hz).

c) Alternative method of preparing the title compound:

As an alternative, the title compound can be prepared by reacting ferrocenyllithium with the compound from example A4.

Ferrocenyllithium is prepared by the method of R. Sanders and U. T. Müller-Westerhoff (J. Organomet. Chem. 1996, 219) from 3.6 g (19 mmol) of ferrocene, 0.26 g (2.3 mmol) of potassium t-butoxide in 180 ml of absolute THF and 24.5 ml (37 mmol) of a 1.5 M solution of t-butyllithium in pentane. A precooled suspension of the compound of example A4 (crude product from a batch starting from 18 mmol of (R,R-N,N'-bis(methoxyethyl)cyclohexane-1,2-diamine) is subsequently added dropwise at −78° C. The reaction mixture is allowed to warm to RT overnight, the LiCl formed is removed by filtration under protective gas and 2.2 ml (22 mmol) of a 10.0 M borane-dimethyl sulfide solution are added at 0° C. Purification by chromatography on an Alox N column [hexane:ethyl acetate (10:1)] and drying in a high vacuum (HV) gives 4.3 g (52%) of the title compound. $^{31}$P-NMR (C$_6$D$_6$, 162 MHz): δ=104.5 (q, J$_{PB}$=87 Hz).

EXAMPLE B4

Preparation of

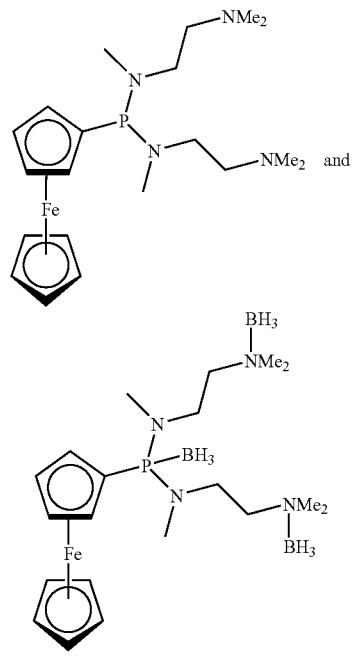

a) Ferrocenyllithium is prepared by the method of R. Sanders and U. T. Müller-Westerhoff (J. Organomet. Chem. 1996, 219) from 1.1 g (5.9 mmol) of ferrocene, 83 mg (0.72 mmol) of potassium t-butoxide in 50 ml of absolute THF and 7.70 ml (12 mmol) of a 1.5 M solution of t-butyllithium in pentane. A precooled suspension of the compound of example A3 (crude product from a batch starting from 11 mmol of N,N',N'-trimethylethylenediamine) is subsequently added dropwise at −78° C. The reaction mixture is allowed to warm to RT overnight, the LiCl formed is removed by filtration and the solvent is distilled off in a high vacuum. This gives 1.5 g of an orange oil which is composed of equal amounts of ferrocene and borane-free title compound (42%). $^{31}$P-NMR (C$_6$D$_6$, 162 MHz): 93.9 (s).

b) 0.11 ml (1.1 mmol) of a 10.0 M borane-dimethyl sulfide solution is added to a solution of 221 mg (0.37 mmol) of the compound prepared as described in step a) in 3 ml of toluene at 0° C. Chromatographic purification on silica gel [eluent=hexane:ethyl acetate (2:1)] and drying in a high vacuum gives 152 mg of the borane-containing title compound as an orange oil. $^{31}$P-NMR (C$_6$D$_6$, 162 MHz): δ=94.6 (q, J$_{PB}$=94 Hz).

EXAMPLE B5

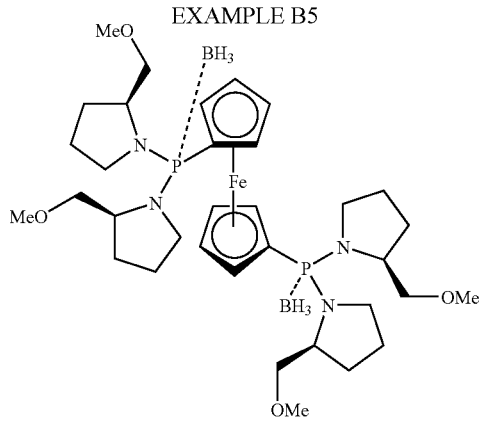

10.95 ml 17.51 mmol) of n-butyllithium (1.6 M in hexane) are added to 2.63 (17.51 mmol)of tetramethylethylenediamine (TMEDA) in 2.5 ml of hexane. A solution of 1.32 g (7.1 mmol) of ferrocene in 59 ml of hexane is added dropwise to the resulting solution while stirring and the reaction mixture is stirred further overnight. The resulting orange-brown reaction mixture is subsequently transferred under argon pressure via a cannula into a vessel containing a solution of 18 mmol of the compound of example A1 in 80 ml of THF which has been cooled to 0-5° C. After stirring overnight at RT, an excess of borane- THF complex (50 mmol, 1 M in THF) is added to the reaction mixture. After stirring for 2 hours, the solvent is distilled off under reduced pressure on a rotary Evaporator. The residue is taken up in water/TBME and extracted a number of times with TBME (tert-butyl methyl ether). The organic phases are dried over sodium sulfate and Evaporated under reducedd pressure on a rotar evaporator. Chromatography on silica gel (eluent: heptane/TBME, 3:1) gives 3.9 g of the title compound as a reddish orange oil (yield: 75%). $^1$H—NMR (C$_6$D$_6$, 300 MHZ, some characteristic signals): 4.81 (m, 4H, cyclopentadiene), 4.62-4.67 (m, 4H, cyclopentadiene), 3.22 (s, 6H, O—CH$_3$), 3.12 (s, 6H, O—CH$_3$).

$^{31}$P—NMR (C$_6$D$_6$, 121 MHz): 79.4 (m, br).

C) Preparation of Metalated Aromatic Monophosphines and Diphosphines

EXAMPLE C1
Preparation of

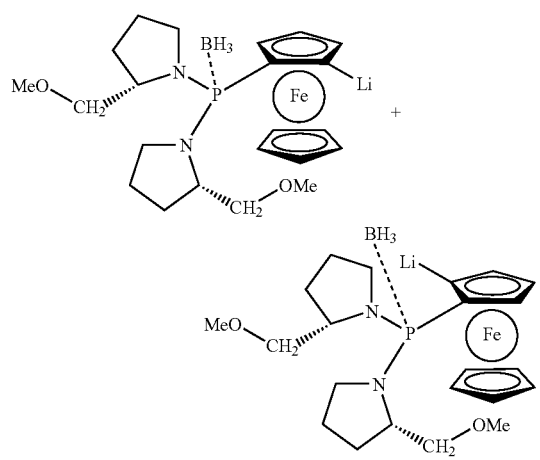

Me = methyl

In a 100 ml round-bottom flask provided with an argon inlet, the compound of example B1 (1.00 g, 2.18 mmol) is dissolved in dry TBME (5.00 ml) and n-hexane (5.00 ml) and the solution obtained is cooled to −30° C. This results in precipitation of the starting material as a yellow solid. sec-Butyllithium (1.3 M in cyclohexane; 1.76 ml, 2.29 mmol, 1.05 equivalents) is added dropwise. During this addition, the yellow solid gradually goes into solution, the solution becomes orange-red and after about 30 minutes an orange solid precipitates. One of the two possible diastereomers is formed preferentially.

Characterization of the Lithiated Title Compound by Means of NMR:

For this purpose, the compound (45 mg, 0.10 mmol) in 1.0 ml of absolute diethyl ether (Et$_2$O) is admixed at −78° C. with 86 μl (0.11 mmol) of a 1.3 M solution of s-butyllithium in cyclohexane:hexane (92:8) and the mixture is stirred at −30° C. for 2 hours. The solvent is distilled off in a high vacuum, the residue is washed 3 times with 3 ml each time of absolute pentane at −30° C., dried in a high vacuum and subsequently dissolved at −30° C. either in 0.7 ml of absolute d$_8$-toluene or in 0.7 ml of absolute d$_{10}$-diethyl ether. After transfer of the solution to an NMR tube, various NMR measurements are carried out.

Characteristic NMR signals in d$_{10}$-Et$_2$O: $^1$H-NMR (500 MHz, 265 K): 3.12/3.25 (each br s, 6H, CH$_3$—O); 4.08 (s, 5H, FcC—H). $^{31}$P{$^1$H}-NMR (162 MHz, 265 K): 88 (mc) ppm. $^7$Li-NMR (194 MHz, 265 K): 2.3 (s) ppm.

After the measurement, the NMR sample is reacted with 1.6 equivalents of trimethylchloro-silane. According to the NMR spectrum, only one of the two possible diastereomeric ortho-substituted compounds is formed.

For the NMR experiments in d$_8$-toluene, 46 μl, (0.31 mmol) of TMEDA are added to the lithiated compound. Characteristic NMR signals:

$^1$H-NMR (500 MHz, 225 K): 3.12/3.30 (each s, 6H, CH$_3$—O; 4.40 (s, 5H, FcC-H). $^{31}$P{$^1$H}-NMR (162 MHz, 190 K): 84 (mc) ppm.

$^7$Li-NMR (194 MHz, 190 K): 2.0 (br s) ppm.

EXAMPLE C2

Preparation of

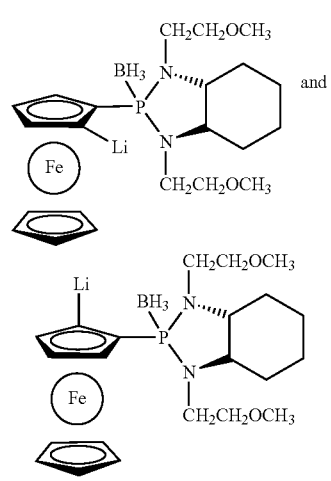

459 mg (1.0 mmol) of the compound of example B3 are dissolved in 10 ml of absolute Et$_2$O. After cooling to —78° C., the starting material partly precipitates and the resulting suspension is reacted with 0.8 (1.1 mmol) of a 1.3 M solution of s-butyllithium in cyclohexane:hexane 992:8). During this addition, the orange solid gradually goes into solution, the solution becomes orange-red and after about 30 minutes and orange solid precipitates. One of the two diaseereomers is formed preferentially.

Characterization of the First Lithiated Title Compound by Means of NMR:

46 mg (0.10 mmol) of the compound in 2.5 ml of absolute Et$_2$O are ortho-lithiated by means of 85 µl (0.11 mmol) of a 1.3 M solution of s-butyllithium in cyclohexane:hexane (92:8). The suspension is evaporated in a high vacuum, the residue is washed 3 times with 3 ml each time of absolute pentane and, after drying in a high vacuum at –30° C., the orange solid is dissolved in 0.7 ml of absolute d$_8$-toluene. After transfer of the solution to an NMR tube, NMR measurements are carried out:

Characteristic NMR Signals:
$^1$H-NMR (500 MHz, 250 K): 3.89 [mc, 1H, FcC—H(lithiated ring)]; 4.19 (s, 5H, FcC—H); 4.65 [mc, 1H, FcC—H (lithiated ring)]; 5.21 [mc, 1H, FcC—H(lithiated ring)] ppm. $^{31}$P{$^1$H}-NMR (162 MHz, 190 K): 132 (mc) ppm. $^7$Li-NMR (194 MHz, 190 K): 2.3 (s) ppm.

After the measurement, the NMR sample is reacted with 1.6 equivalents of trimethylchloro-silane. According to the NMR spectrum, only one of the two possible diastereomeric ortho-substituted compounds is formed.

EXAMPLE C3

Preparation of

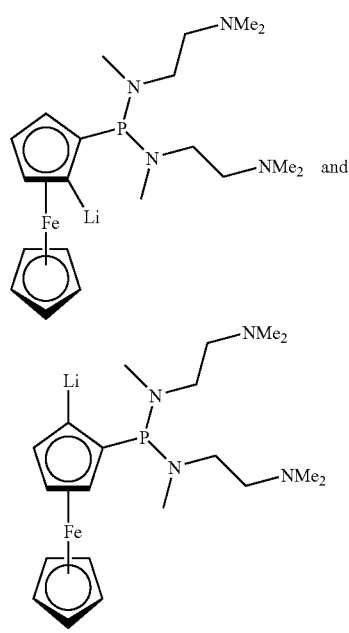

A solution of 0.14 mmon of the compound of example B5 in 1.0 ml of diethyl ether is Cooled to —78° C. This results in the starting material partly precipitating as a light-yellow Solid. The suspension is admixed with 0.10 ml (0.14 mmol) of a 1.3 M solution of s-butyllithium in cyclohexane:hexane (92:8). The mixture is subsequently stirred at —25° C. for 2 hours. This results in formation of a dark red solution.

When this reaction mixture is reacted with 32 µl (0.22 mmol) of trimethylchlorosilane, the compound silylated in the ortho position is obtained in a yield of more than 80%.

D) Preparation of Ortho-Substituted Monophosphines and Diphosphines

EXAMPLE D1

Preparation of

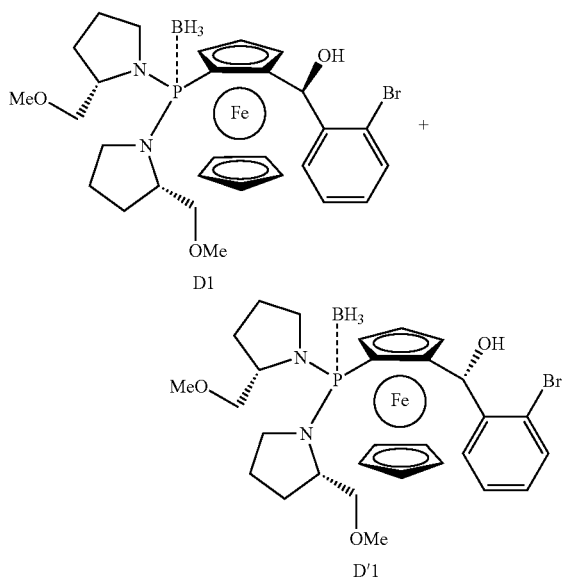

The suspension from example C1 is stirred for 2 hours and 2-bromobenzaldehyde (485 mg, 2.62 mmol, 1.2 equivalents) is then added dropwise at –30° C., the cooling bath is then removed and the suspension is stirred overnight (14 h) while warming to RT. The reaction mixture is hydrolyzed with saturated NH$_4$Cl solution, TBME (100 ml) is added and the organic phase is then separated off and dried over Na$_2$SO$_4$. The solvent is distilled off on a rotary evaporator and the crude product is purified by column chromatography (200 g of silica gel, n-heptane/TBME 5:1). The ferrocenyl alcohol D1 (849 mg, 1.32 mmol, 61%) and the ferrocenyl alcohol D'1 (334 mg, 0.52 mmol, 24%) are obtained as orange-brown solids. Furthermore, the unreacted compound of example B1 (150 mg, 0.33 mmol, 15%) is recovered in the form of a brown oil. $^{31}$P-NMR (C$_6$D$_6$, 121 MHz): 73.3 (m, br).

EXAMPLE D2

Preparation of

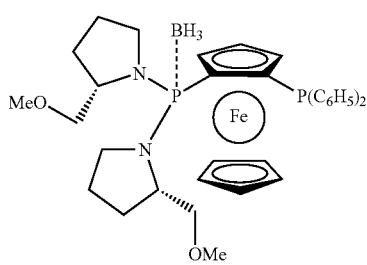

In a 50 ml round-bottom flask provided with an argon inlet, the compound of example B1 (104 mg, 0.23 mmol) is dissolved in dry TBME (1.00 ml) and n-hexane (1.00 ml) and the solution obtained is cooled to −30° C. This results in the starting material precipitating as a yellow solid. sec-Butyllithium (1.3 M in cyclohexane; 0.18 ml, 0.24 mmol, 1.05 equivalents) is added dropwise. During this addition, the yellow solid gradually goes into solution, the solution becomes orange-red and after about 30 minutes an orange solid precipitates (compound of example C1). After stirring at −30° C. for 3 hours, chlorodiphenylphosphane (61 mg, 0.28 mmol, 1.2 equivalents) is added dropwise, the cooling bath is removed and the solution is stirred overnight (14 h) while warming to RT. The reaction mixture is hydrolyzed with saturated NH$_4$Cl solution (10 ml), TBME (20 ml) is added, the organic phase is separated off and dried over Na$_2$SO$_4$. The solvent is distilled off on a rotary evaporator and the crude product is purified by column chromatography (60 g of silica gel, n-heptane/TBME 5:1). The title compound (142 mg) is obtained in the form of a brown oil which is still contaminated with the starting compound of example B1. The isolated oil crystallizes after some time when left to stand in air to give a brown solid. $^{31}$P-NMR (C$_6$D$_6$, 121 MHz): 77.9 (m, br), −25.1 (s).

EXAMPLE D3

Preparation of

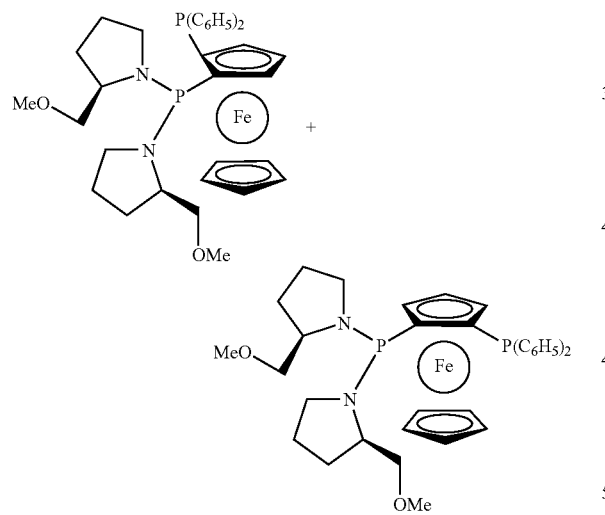

0.59 mmol of a 1.3 molar s-butyllithium solution in cyclohexane is slowly added dropwise to a solution of 200 mg (0.45 mmol) of the compound of example B2 in 1 ml of TBME and 1 ml of hexane at −30° C. and the red solution is stirred at this temperature for 2 hours. 0.11 ml (0.59 mmol) of Cl-phenyl$_2$ is then added. The resulting orange suspension is stirred at -30° C. for 2 hours and the temperature is subsequently allowed to rise to room temperature. 2 ml of saturated NaHCO$_3$ and 2 ml of TBME are added to the mixture and the mixture is stirred. After filtration through Celite, washing of the organic phase with 3×5 ml of water and drying over Na$_2$SO$_4$, the solvent is removed on a rotary evaporator. Chromatography (silica gel 60 from Fluka, eluent =hexane/ethyl acetate 2:3 and 3% of Nethyl$_3$) gives an orange oil which, according to NMR, comprises predominantly one of the two possible diastereomers.

$^{31}$P-NMR (C$_6$D$_6$, 121 MHz): 68.4 (d, J 73 Hz), −23.5 (d, J 73 Hz). $^1$H-NMR (C$_6$D$_6$, 300 MHz, some characteristic signals): 4.114 (s, 5H, cyclopentadiene), 3.114 (s, 3H, O—CH$_3$), 3.27 (s, 3H, O—CH$_3$).

EXAMPLE D4

Preparation of

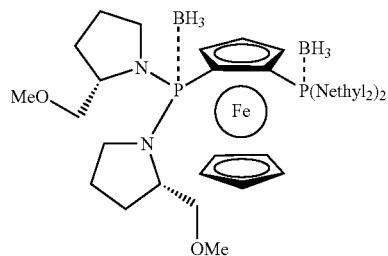

In a 50 ml round-bottom flask provided with an argon inlet, the compound of example B1 (1.00 g, 2.18 mmol) is dissolved in dry TBME (5.00 ml) and n-hexane (5.00 ml) and the solution obtained is cooled to −30° C. This results in precipitation of the starting material as a yellow solid. s-Butyllithium (1.3 M in cyclohexane; 1.76 ml, 2.29 mmol, 1.05 equivalents) is added dropwise. During this addition, the yellow solid gradually goes into solution, the solution becomes orange-red and after about 30 minutes an orange solid precipitates (compound of example C1). After stirring at −30° C. for 2 hours, ClP(Nethyl$_2$)$_2$ (551 mg, 2.62 mmol, 1.2 equivalents) is added dropwise, the cooling bath is removed and the suspension is stirred for 2 hours while warming to RT. BH$_3$-Smethyl$_2$ (0.25 ml, 2.62 mmol, 1.2 equivalents) is subsequently added dropwise and the suspension is stirred overnight (14 h) at RT. The reaction mixture is hydrolyzed with saturated NaCl solution (50 ml), TBME (50 ml) is added and the organic phase is separated off and dried over Na$_2$SO$_4$. The solvent is distilled off on a rotary evaporator and the crude product is purified by column chromatography (100 g of silica gel, n-heptane/TBME 5:1). The title compound (1.10 g, 1.71 mmol, 78%) is obtained in the form of an orange solid. $^{31}$P-NMR (C$_6$D$_6$, 121 MHz): 99.7-99.0 (m, br), 79.9-79.5 (m, br).

EXAMPLE D5

Preparation of

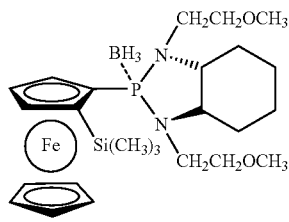

The compound B3 (45.6 mg, 0.10 mmol) and 2 ml of absolute diethyl ether (Et$_2$O) are placed in a reaction vessel at 0° C. and sec-butyllithium (1.3 M in cyclohexane/hexane, 77 µl, 0.10 mmol) is slowly added dropwise. After 2 hours at 0° C., chlorotrimethylsilane (21 µl, 0.16 mmol) is added slowly and the mixture is subsequently allowed to warm to room temperature overnight. Evaporation in a high vacuum (HV) and chromatographic purification (eluent:hexane/ethyl acetate 7:1) gives the title compound in a yield of 81%. Virtually only one of two possible diastereomers is obtained. Characteristic NMR signals:

$^1$H-NMR (C$_6$D$_6$, 400 MHz): δ=4.19 (s, 5H, Cp-H); 0.38 (s, 9H, (CH$_3$)$_3$Si).
$^{31}$P-NMR (C$_6$D$_6$, 162 MHz):=109.6 ppm.

EXAMPLE D6

Preparation of

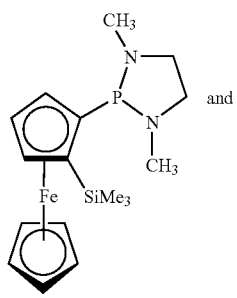
(2)

and

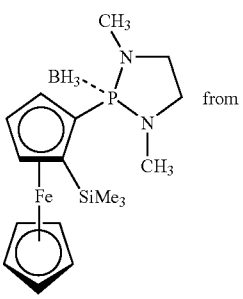
(3)

from

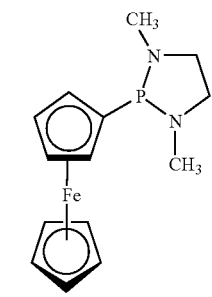
(1)

The starting material (1) is prepared as described in the literature: Nifant'ev I.E., Boricenko A.A., Phosphorus, Sulfur and Silicon 1992, 68, 99.

Compound (1) (60.5 mg, 0.20 mmol) and 2 ml of absolute Et$_2$O are placed in a reaction vessel at −78° C. t-Butyllithium (1.5 M in pentane, 130 μl, 0.19 mmol) is then slowly added dropwise. After 20 minutes at −78° C., the mixture is stirred at −25° C. for a further three hours and then cooled back down to −78° C., after which trimethylchlorosilane (42 μl, 0.32 mmol) is added slowly. The mixture is subsequently allowed to warm to room temperature overnight and is evaporated in a high vacuum to give compound 1.

To confirm the compound (2), it is converted by means of borane into the protected and stable compound (3). After protection by means of borane, the reaction mixture is purified on a silica gel column using hexane/ethyl acetate (5:1) as eluent. Compound (3) is obtained as an orange solid (conversion of >60% according to $^{31}$P-NMR).

$^1$H-NMR (400 MHz, C$_6$D$_6$, 295 K): 0.33 (s, 9H, (CH$_3$)Si); 1.54 (q, J=92 Hz, 3H, BH$_3$); 2.32 (d, J=11 Hz, 3H, CH$_3$—N); 2.45-2.53 (m, 1H, CH$_2$—N); 2.54 (d, J=12 Hz, 3H, CH$_3$—N); 2.45-2.64 (m, 2H, CH$_2$—N); 2.67-2.75 (m, 1H, CH$_2$—N); 4.18 (ddd, J=2.4 Hz, 1.3 Hz, JHP very small, 1 H, CH(3)); 4.20 (s, 5H, Cp); 4.27 (td, J=2.4 Hz, 1.2 Hz, 1H, CH(4)); 4.79 (td =ddd, J=2.4 Hz, 2.4 Hz, 1.3 Hz, 1H, CH(5)) ppm.
$^{13}$C-NMR (126 MHz, C$_6$D$_6$, 295 K): 1.5.((CH$_3$)$_3$Si ); 33.4 (d, J=7 Hz, CH$_3$—N); 35.6 (d, J=8 Hz, CH$_3$—N); 50.3/51.6 (each s, CH$_2$—N); 70 (Cp); 72.7 (d, J=8 Hz, C(2)); 73.3 (d, J=9 Hz, CH(4)); 78.5 (d, J=47 Hz, C(1)); 78.7 (d, J=20 Hz, CH(5)); 79.7 (d, J=8 Hz, CH(3)) ppm.
$^{31}$P-NMR (162 MHz, C$_6$D$_6$, 295 K): 112.6 (q, J$_{PB}$ 75Hz).

EXAMPLE D7

Preparation of

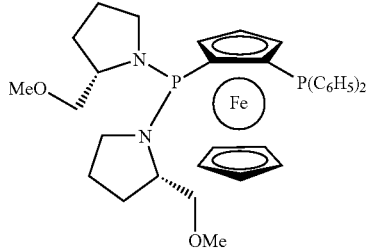

1.2 g (1.87 mmol) of the compound of example D2 are refluxed in 6 ml of diethylamine for 21 hours. Volatile constituents are then removed on a rotary evaporator. The residue is treated 3 times with 2-3 ml each time of diethylamine, refluxed for one hour and the diethylamine is taken off again. 3-5 ml of TBME are subsequently added 3 times to the residue, stirred and the TBME is taken off at 48° C. in a high vacuum. The product is obtained virtually quantitatively as an orange oil.

$^{31}$P—NMR (C$_6$D$_6$, 121 MHz): 68.4 (d), —23.5 (d), Jpp 73 Hz) $^1$H—NMR (C$_6$D$_6$, 300 MHz, some chatracteristic signals): 4.114 (s, 5H, cyclopentadiene), 3.114 (s, 3H, O—CH$_3$), 3.27 (s, 3H, O—CH$_3$).

EXAMPLE D8

Preparation of

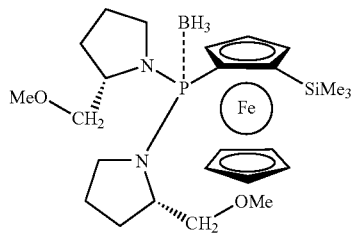

1.2 equivalents of a 1.3 M solution of s-butyllithium in cyclohexane:hexane (92:8) are added dropwise to a solution of 0.09 mmol of the compound of example B1 in 1.0 ml of diethyl ether at —78° C. After stirring at —30° C. for 2 hours, 1.6 equivalents of trimethylchlorosilane are added. According to NMR, the product comprises 93% of ortho-substituted compound and 7% of starting material. Purification on a silica gel column (eluent: hexane:ethyl acetate (10:1)) gives the title compound as an orange solid. Characteristic NMR signals: $^1$HF—NMR (500 MHz, $C_6D_6$, 295 K): 0.45 (s, 9H, Si$(CH_3)_3$); 3.07/3.29 (each s, 6H, $CH_3$—O; 4.42 (s, 5H, FcC—H) ppm. $^{31}P\{^1H\}$—NMR (162 MHz, $C_6D_6$, 295 K): 73.6 (mc) ppm.

EXAMPLE D9

Preparation of

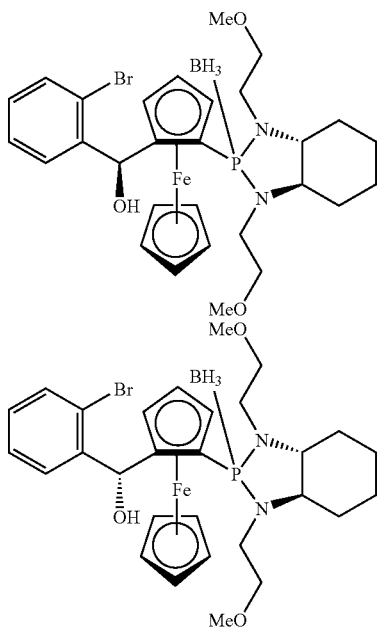

459 mg (1.0 mmol) of the compound of example B3 in 10 ml of absolute $Et_2$O are reacted with 0.85 ml (1.1 mmol) of a 1.3 M solution of s-butyllithium in cyclohexane: hexane (92: 8) at —78° C., the mixture is stirred at 0° C. for 2 hours and a solution of 0.14 ml (1.2 mmol) of 2-bromobenzaldehyde in 5 ml of absolute $Et_2O$ is subsequently added dropwise. After warming to RT overnight, the mixture is hydrolyzed with saturated $NH_4Cl$ solution, the phases are separated, the aqueous phase is extracted with dichloromethane and the combined organic phases are washed with saturated NaCl solution. Drying over $MgSO_4$ and evaporation on a rotary evaporator gives a (73:27) mixture of the diastereomers which can be separated from one another by chromatographic purification on silica gel [eluent: pentane: $Et_2O$ (2:1)]. This gives 314 mg (49%) of one diastereomer and 125 mg (19%) of the other diastereomer as dark orange crystals. Characterization of the main fraction (characteristic NMR signals): $^1$H—NMR (400 MHz, $C_6D_6$, 295 K): 3.05/3.19 (each s, 6H, $CH_3$—O); 3.66 (s, 1H, CH—O); 4.39 (s, 5H, FcC—H); 5.98 (s, 1H, OH). $^{13}C\{^1H\}$—NMR (100 MHz, $C_6D_6$, 295 K): 69.6 (s, 1C, CH—O); 70.6 (s, 5C, FcC—H). $^{31}P\{^1H\}$—NMR (162 MHz, $C_6D_6$, 295 K): 113.0 (mc) ppm.

Characterization of the secondary fraction (characteristic NMR signals): $^1$H—NMR (400 MHz, $C_6D_6$, 295 K): 2.93/ 3.21 (each s, 6H, $CH_3$—O); 4.22 (s, 5H, FcC—H); 4.35 (d, $^3J$=3.4 Hz, 1H, CH—O); 6.50 (d, $^3J$=3.4 Hz, 1H, OH). $^{13}C\{^1H\}$-NMR (100 MHz, $C_6D_6$, 295 K): 70.0 (s, 1 C, CH—O); 71.4 (s, 5C, FcC—H). $^{31}P\{^1H\}$-NMR (162 MHz, $C_6D_6$, 295 K): 108.2 (mc) ppm.

EXAMPLE D10

Preparation of

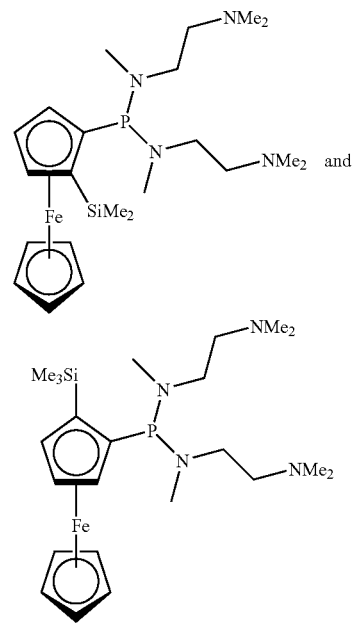

A solution of 0.14 mmol of the compound of example B4 in 1.0 ml of diethyl ether is cooled to —78° C. and admixed with 0.10 ml (0.14 mmol) of a 1.3 M solution of s-butyllithium in cyclohexane:hexane (92:8). The mixture is subsequently stirred at —25° C. for 2 hours. 32 µl (0.22 mmol) of trimethylchlorosilane are added to the resulting dark red solution and the reaction mixture is stirred at room temperature for one hour. For the purification and characterization, the compound is protected by means of borane. For this purpose, 0.5 mmol of a 10.0 M borane-dimethyl sulfide solution are added. 83% of ortho-substituted compound and 17% of starting material are obtained. Both compounds are protected by borane.

Characteristic NMR signals of the borane-protected ortho-substituted compound: $^1$H—NMR (400 MHz, $C_6D_6$, 295 K): 0.43 (s, 9H, Si$(CH_3)_3$); 4.15-4.19 (m, 1H, FcC—H); 4.25-4.30 (m, 2H, FcC—H); 4.32 (s, 5H, FcC—H) ppm. $^{31}P\{^1H\}$-NMR (162 MHz, $C_6D_6$, 295 K): 93.9 ppm (q, $^1J_{PB}$=87 Hz).

EXAMPLE D12

Preparation of

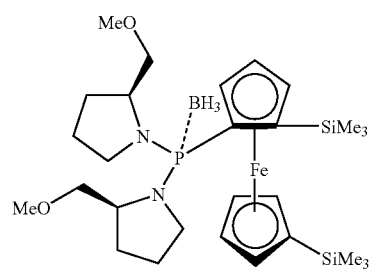

0.77 ml (0.59 mmol) of a 1.3 molar s-butyllithium solution is added dropwise to an orange suspension of 153 mg (0.33 mmol) of the compound B1 in 4 ml of TBME/hexane 1:1 at −30° C. The reaction mixture is stirred at this temperature for 3 hours. During this time, an orange solution is formed first and this then changes back into a suspension. 0.15 ml (1.17 mmol) of chlorotrimethylsilane is subsequently added dropwise at −30° C. The cooling is removed, the reaction mixture is stirred overnight at room temperature and subsequently extracted a number of times in water/TBME. The organic phases are collected, dried over sodium sulfate and evaporated under reduced pressure on a rotary evaporator.

Chromatography on silica gel 60 (eluent:heptane/TBME 20:1) gives the title compound in good yield as an orange solid. $^{3}$P-NMR (C$_6$D$_6$, 121 MHz): 77.9 (m,br). $^1$H-NMR (C$_6$D$_6$, 300 MHz, some characteristic signals): 3.29 (s, 3H, O—CH$_3$), 3.07 (s, 3H, O—CH$_3$), 0.49 (s, 9H, SiMe$_3$), 0.26 (s, 9H, SiMe$_3$).

EXAMPLE D13

Preparation of

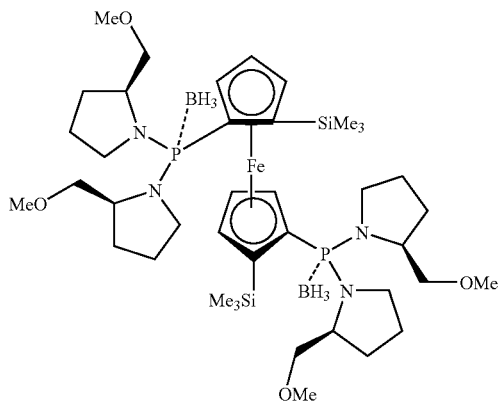

0.45 ml (0.58 mmol) of a 1.3 molar s-butyllithium solution is added dropwise to an orange solution of 204 mg (0.28 mmol) of the compound of example B6 in 4 ml of TBME/hexane 1:1 at −30° C. The reaction mixture is stirred at this temperature for 3 hours. During this time, it becomes red and a small amount of a red substance precipitates. The mixture is subsequently cooled to −40° C. and 0.11 ml (0.84 mmol) of chlorotrimethylsilane is added dropwise. The cooling is removed, the reaction mixture is stirred overnight at room temperature and extracted a number of times in water/TBME. The organic phases are collected, dried over sodium sulfate and evaporated under reduced pressure on a rotary evaporator. Chromatography on silica gel 60 (eluent: methylene chloride) gives the title compound in good yield as an orange solid. Characteristic NMR signals: $^{31}$P-NMR (C$_6$D$_6$, 121 MHz): 78.7 (m,br). $^1$H-NMR (C$_6$D$_6$, 300 MHz, some characteristic signals): 5.86 (m, 2H), 5.08 (m, 2H), 3.33 (s, 6H, O—CH$_3$), 3.06 (s, 6H, O—CH$_3$), 0.56 (s, 18H, SiMe3).

EXAMPLE D14

Preparation of

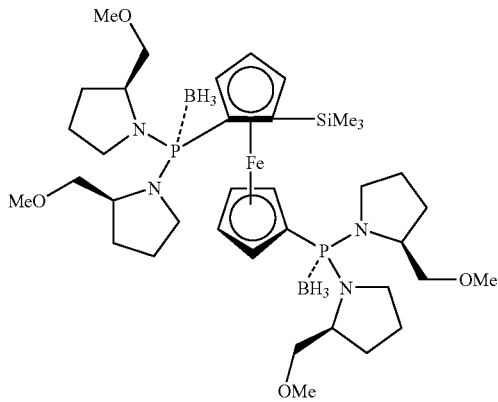

0.23 ml (0.29 mmol) of a 1.3 molar s-butyllithium solution is added dropwise to an orange solution of 203 mg (0.28 mmol) of the compound of example B6 in 4 ml of TBME/hexane 1:1 at −30° C. The reaction mixture is stirred at this temperature for 3 hours. The resulting orange suspension is subsequently cooled to −40° C. and 0.22 ml (0.42 mmol) of chlorotrimethylsilane is added dropwise. The cooling is removed, the reaction mixture is stirred overnight at room temperature and subsequently extracted a number of times in water/TBME. The organic phases are combined, dried over sodium sulfate and evaporated under reduced pressure on a rotary evaporator. Chromatography on silica gel 60 (eluent: methylene chloride) gives the title compound in good yield as an orange, virtually solid oil. $^{31}$P-NMR (C$_6$D$_6$, 121 MHz): 80.0 (m,br), 77.1 (m,br). $^1$H-NMR (C$_6$D$_6$, 300 MHz, some characteristic signals): 3.35 (s, 3H, O—CH$_3$), 3.23 (s, 3H, O—CH$_3$), 3.11 (s, 3H, O—CH$_3$), 3.05 (s, 3H, O—CH$_3$), 0.51 (s, 9H, SiMe3).

EXAMPLE D15

Preparation of

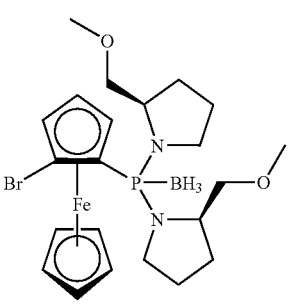

In a 50 ml round-bottom flask provided with an argon inlet, compound B1 (1.00 g, 2.18 mmol) is dissolved in dry TBME (5.00 ml) and n-hexane (5.00 ml) and the solution obtained is cooled to −30° C. This results in precipitation of the starting material as a yellow solid. s-Butyllithium (1.3 M in cyclohexane; 1.76 ml, 2.29 mmol, 1.05 equivalents) is added dropwise. During this addition, the yellow solid gradually goes into solution, the solution becomes orange-red and after about 30 minutes an orange solid precipitates. After stirring at −30° C. for 2 hours, BrF$_2$C—CF$_2$Br (680 mg, 2.62 mmol, 1.2 equivalents) is added dropwise, the cooling bath is removed and the suspension is stirred for 2 hours while warming to RT. The reaction mixture is evaporated to dryness in a high vacuum on a rotary evaporator and used further in step b) without purification. $^{31}$P-NMR (C$_6$D$_6$, 121 MHz): 76.5 (m).

E) Preparation of Diphosphines

EXAMPLE E1

Preparation of

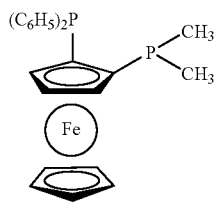

a) Preparation of

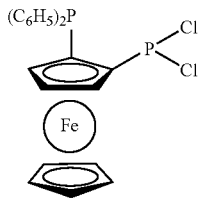

4 equivalents of HCl in the form of a 2 molar HCl/diethyl ether solution are added to a solution of 1.10 g (1.75 mmol) of the compound of example D2 (which has previously been freed of the borane by treatment with diethylamine in a manner analogous to that described in example D8) in 20 ml of TBME at 0° C. while stirring, resulting in formation of a precipitate. After stirring at 0° C. for a further hour, this precipitate is filtered off under argon and washed a number of times with TBME. The filtrate is evaporated in a high vacuum and the orange product is characterized by means of NMR.

$^{31}$P-NMR (C$_6$D$_6$, 121 MHz): 161.6 (d), −24.6 (d), J$_{pp}$ 170 Hz);

$^1$H-NMR (C$_6$D$_6$, 300 MHz, characteristic signals): 3.89 (s, 5H, cyclopentadiene).

The product obtained is used in the subsequent step b) without purification.

b) Preparation of the title compound

The product obtained as described in step a) is dissolved in 10 ml of THF and admixed at −40° C. with a methylmagnesium chloride solution until the desired product has been formed quantitatively according to $^{31}$P-NMR (2 to 4 equivalents). After work-up and chromatography, the product is isolated as an orange solid. The NMR spectra correspond to the spectra reported in the literature (Kagan et al. in Eur. J. Org. Chem. (2000) 2893-9).

EXAMPLE E2

Preparation of

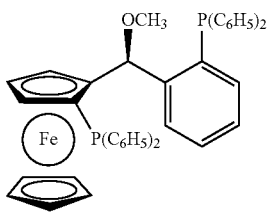

a) Preparation of

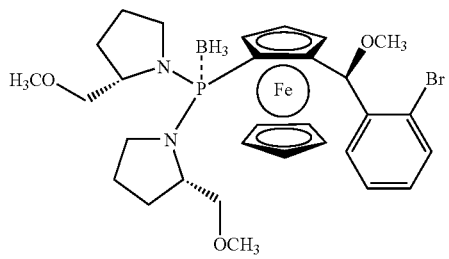

In a 50 ml round-bottom flask provided with an argon inlet, potassium hydride (32 mg, 0.79 mmol), 1.3 equivalents) is suspended in dry THF (0.50 ml) under argon and cooled to 0° C. A solution of compound D1 from example D1 (390 mg, 0.61 mmol) in THF (3.5 ml) is slowly added dropwise, resulting in virtually all of the potassium hydride going into solution. The orange suspension obtained is stirred at RT for 1.5 hours and subsequently cooled back down to 0° C. Methyl iodide (95 mg, 0.67 mmol, 1.10 equivalents) is added dropwise. During the addition, formation of a white precipitate is observed. The suspension is stirred at 0C for 10 minutes and at RT for 1 hour. The suspension is admixed with TBME (10 ml) and hydrolyzed with water (10 ml). The organic phase is separated off and dried over Na$_2$SO$_4$. The solvent is distilled off on a rotary evaporator and the crude product (yellow solid) is purified by column chromatography (150 g of silica gel, n-heptane/TBME 5:1→3:1). The compound (363 mg, 0.55 mmol, 91%) is obtained as an orange-yellow solid. $^{31}$P-NMR (C$_6$D$_6$, 121 MHz): 75.3 (m, br).

b) Preparation of

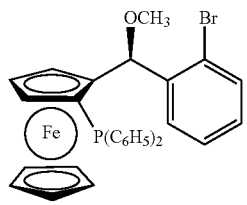

In a 100 ml round-bottom flask provided with an argon inlet, the compound prepared as described in step a) (500 mg, 0.76 mmol) is dissolved in diethylamine (3.00 ml) under argon and stirred overnight (14 h) at 50° C. All volatile constituents are subsequently removed at 50° C. in an oil pump vacuum. The residue obtained (orange-brown oil) is dissolved 3 times in dry TBME (2.00 ml each time) and all volatile constituents are removed at 50° C. in an oil pump vacuum. The residue (orange-brown oil) is dissolved in dry TBME (10 ml) and the solution is cooled to 0° C. An HCl solution (2 M in diethyl ether; 1.52 ml, 3.04 mmol, 4.00 equivalents) is added dropwise, resulting in formation of a white precipitate. After stirring at 0° C. for 20 minutes, the suspension is filtered under argon by means of a double-ended frit filter. The yellow filtrate obtained is cooled to −30° C. and phenylMgCl solution (2 M in THF; 3.80 ml, 7.60 mmol, 10.00 equivalents) is added dropwise. The reaction mixture is stirred for 3 days while warming to RT and hydrolyzed with saturated NH$_4$Cl solution (10 ml). The organic phase is separated off, the aqueous phase is extracted with TBME (50 ml), the combined organic phases are dried over Na$_2$SO$_4$ and the solvent is distilled off on a rotary evaporator. The crude product is purified by column chromatography (100 g of silica gel, n-heptane/TBME 20:1). The title compound is obtained as a yellow solid. $^{31}$P-NMR (C$_6$D$_6$, 121 MHz): −20.5 (s).

EXAMPLE E3

Preparation of

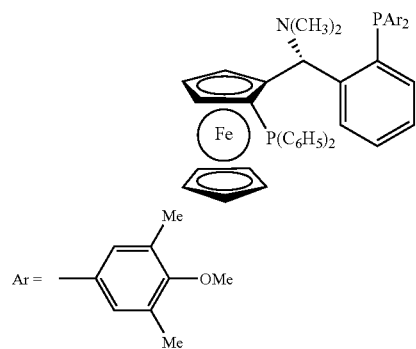

a) Preparation of

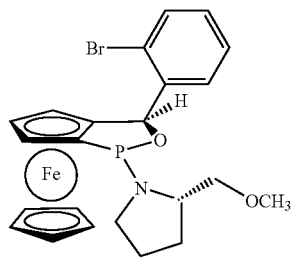

In a 100 ml round-bottom flask provided with an argon inlet, compound D'1 from example D1 (500 mg, 0.78 mmol) is dissolved in diethylamine (3.00 ml) under argon and the mixture is stirred overnight (14 h) at 50° C. All volatile constituents are subsequently removed at 50° C. in an oil pump vacuum. The residue obtained (orange-brown oil) is dissolved 3 times in diethylamine (2.00 ml each time), the solution is stirred at 50° C. for 30 minutes and all volatile constituents are removed at 50° C. in an oil pump vacuum. The residue (orange-brown oil) is dissolved twice in dry TBME (2 ml) and all volatile constituents are removed at 50° C. in an oil pump vacuum. The compound (401 mg, 0.78 mmol) is obtained in a quantitative yield as an orange-brown oil. The compound is used in the next step without further purification. $^{31}$P-NMR (C$_6$D$_6$, 121 MHz): 107.7 (s).

b) Preparation of

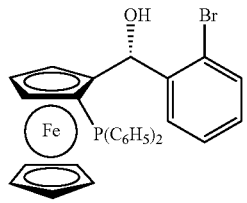

In a 100 ml round-bottom flask provided with an argon inlet, the compound prepared as described in step a) (401 mg, 0.78 mmol) is dissolved in dry TBME (10 ml) and the solution is cooled to 0° C. HCl solution (2 M in diethyl ether; 1.56 ml, 3.11 mmol, 4.00 equivalents) is added dropwise, resulting in formation of a white precipitate. After stirring at 0° C. for 30 minutes, the suspension is filtered under argon by means of an immersion frit. The precipitate obtained is washed with dry TBME (10 ml). The yellow filtrate is evaporated to dryness in an oil pump vacuum and the residue obtained is dissolved in dry TBME (5.00 ml) and THF (5.00 ml). The solution is cooled to −30° C. and phenylMgBr solution (1 M in THF; 3.89 ml, 3.89 mmol, 5.00 equivalents) is added dropwise. The reaction mixture is stirred overnight (14 h) while warming to RT and hydrolyzed with saturated NH$_4$Cl solution (10 ml).

The organic phase is separated off, the aqueous phase is extracted with TBME (100 ml), the combined organic phases are dried over Na$_2$SO$_4$ and the solvent is distilled off on a rotary evaporator. The crude product is purified by column chromatography (150 g of silica gel, n-heptane/TBME 5:1). The compound is obtained as a yellow solid. $^{31}$P-NMR (C$_6$D$_6$, 121 MHz): −21.5 (s).

c) Preparation of

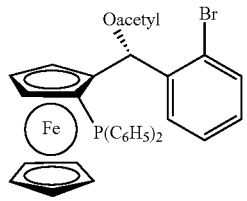

In a 50 ml Schlenk tube, the compound prepared as described in step b) (100 mg, 0.18 mmol) is dissolved in pyridine (1.00 ml) under argon and acetic anhydride (0.50 ml, 4.53 mmol) is added. The orange-brown solution is stirred overnight (15 h) at RT. All volatile constituents are subsequently evaporated in an oil pump vacuum. The compound (108 mg, 0.18 mmol) is obtained in quantitative yield as a brown solid. $^{31}$P-NMR (C$_6$D$_6$, 121 MHz): −23.0 (s).

d) Preparation of

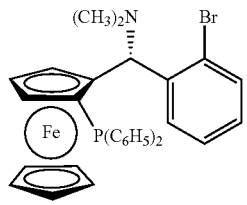

In a 50 ml Schlenk tube, the compound prepared as described in step c) (108 mg, 0.18 mmol) is dissolved in acetonitrile (2.00 ml) under argon and methyl$_2$NH solution (40% in water; 1.00 ml) and water (0.20 ml) are added. The brownish orange solution obtained is stirred overnight (14 h) at 90° C. The solvent is evaporated in an oil pump vacuum, the residue is taken up in CH$_2$Cl$_2$, washed with saturated NaCl solution, the organic phase is separated off and dried over Na$_2$SO$_4$. The solvent is distilled off on a rotary evaporator. The crude product is purified by column chromatography (50 g of silica gel, n-heptane/TBME 3:1). The compound (68 mg, 0.12 mmol, 67%) is obtained as a yellow solid. $^{31}$P-NMR (C$_6$D$_6$, 121 MHz): −24.5 (s).

e) Preparation of the title compound

In a 50 ml Schlenk tube, the compound prepared as described in step d) (50 mg, 0.09 mmol) is dissolved in dry THF (1.00 ml) under argon and the light-yellow solution is cooled to −78"C. t-Butyllithium (1.5 M in pentane; 0.11 ml, 0.17 mmol, 2.00 equivalents) is added dropwise. The solution becomes orange during the addition. After stirring at −78° C. for 15 minutes, chlorobis(3,5-dimethyl4-methoxyphenyl)phosphane (35 mg, 0.10 mmol, 1.20 equivalents) is slowly added dropwise, resulting in the solution becoming yellowish orange. The cooling bath is removed, the reaction mixture is stirred at RT for one hour and subsequently hydrolyzed with saturated NH$_4$Cl solution (10 ml). The organic phase is separated off, the aqueous phase is extracted with TBME (50 ml), the combined organic phases are dried over Na$_2$SO$_4$ and the solvent is distilled off on a rotary evaporator. The crude product is purified by column chromatography (50 g of silica gel, n-heptane/TBME 2:1). The title compound (34 mg, 0.042 mmol, 47%) is obtained as a yellow solid.

$^{31}$P-NMR (C$_6$D$_6$, 121 MHz): −18.4 (d), −25.5 (d).

EXAMPLE E4

Preparation of

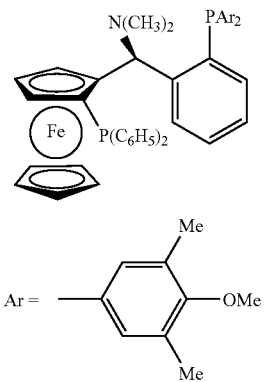

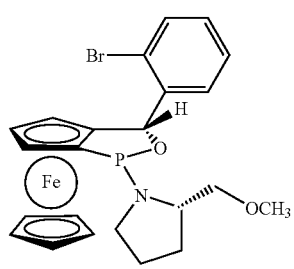

a) Preparation of

In a 100 ml round-bottom flask provided with an argon inlet, compound D1 from example D1 (500 mg, 0.78 mmol) is dissolved in diethylamine (5.00 ml) under argon and the mixture is stirred overnight (14 h) at 50° C. All volatile substituents are subsequently removed at 50° C. in an oil pump vacuum. The residue obtained (orange-brown oil) is dissolved 3 times in diethylamine (3.00 ml each time), the solution is stirred at 50° C. for 30 minutes and all volatile constituents are removed at 50° C. in an oil pump vacuum. The residue (orange-brown oil) is dissolved twice in dry TBME (2 ml) and all volatile constituents are removed at 50° C. in an oil pump vacuum. The compound (1.60 g, 3.11 mmol) is obtained in quantitative yield as an orange-brown oil. The compound is used in the next step without further purification. $^{31}$P-NMR (C$_6$D$_6$, 121 MHz): 109.0 (s).

b) Preparation of

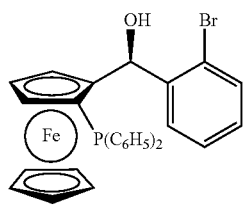

In a 100 ml round-bottom flask provided with an argon inlet, the compound prepared as described in step a) (1.60 g, 3.11 mmol) is dissolved in dry TBME (40 ml) and the solution is cooled to 0° C. HCl solution (2 M in diethyl ether; 6.22 ml, 12.44 mmol, 4.00 equivalents) is added dropwise, resulting in formation of a white precipitate. After stirring at 0° C. for 30 minutes, the suspension is filtered under argon by means of an immersion frit. The precipitate obtained is washed with dry TBME (20 ml). The yellow filtrate is evaporated to dryness in an oil pump vacuum and the residue obtained is dissolved in dry THF (10.00 ml). The solution is cooled to −30° C. and phenylMgBr solution (1 M in THF; 15.55 ml, 15.55 mmol, 5.00 equivalents) is added dropwise. The reaction mixture is stirred overnight (14 h) while warming to RT and hydrolyzed with saturated NH$_4$Cl solution (50 ml). The organic phase is separated off, the aqueous phase is extracted with TBME (100 ml), the combined organic phases are dried over Na$_2$SO$_4$ and the solvent is distilled off on a rotary evaporator. The crude product is purified by column chromatography (150 g of silica gel, n-heptane/TBME 5:1). The compound (801 mg, 1.44 mmol, 46%) is obtained as a yellow solid. $^{31}$P-NMR (C$_6$D$_6$, 121 MHz): −21.8 (s).

c) Preparation of

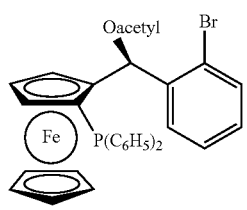

The preparation is carried out as in step c) of example E3.

d) Preparation of

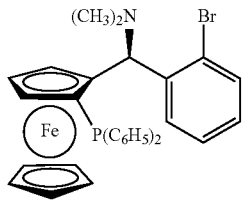

The preparation is carried out as in step d) of example E3.

e) Preparation of the title compound

The preparation is carried out as in step e) of example E3.

The invention claimed is:

1. A process for preparing ferrocene, bisindenylferrocene or ruthenocene having a structural element of the formula I in the aromatic hydrocarbon ring,

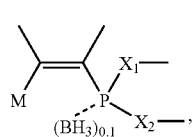 (I)

where
M is —Li, —MgX$_3$, (C$_1$-C$_{18}$-alkyl)$_3$Sn—, —ZnX$_3$ or —B(O—C$_1$-C$_4$-alkyl)$_2$,
X$_1$ and X$_2$ are each, independently of one another, O or N and C-bonded hydrocarbon or heterohydrocarbon radicals are bound to the free bonds of the O or N atoms, the group —C=C— together with carbon atoms forms a hydrocarbon aromatic and
X$_3$ is Cl, Br or I, characterized in that ferrocene, bisindenylferrocene or ruthenocene having a structural element of the formula II in the aromatic ring,

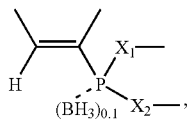 (II)

where X$_1$ and X$_2$ are as defined above and the group —C=C— together with carbon atoms forms a hydrocarbon aromatic,
is reacted with at least equivalent amounts of alkyllithium, a magnesium Grignard compound or an aliphatic Li sec-amide or X$_3$Mg sec-amide, and, to prepare compounds of the formula I in which M is —MgX$_3$, (C$_1$-C$_{18}$-alkyl)$_3$Sn—, —ZnX$_3$ or —B(O—C$_1$-C$_4$-alkyl)$_2$, a lithium compound of the formula Ia,

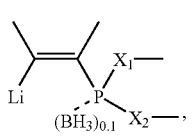 (Ia)

is reacted with at least equivalent amounts of Mg(X$_3$)$_2$, Zn(X$_3$)$_2$,(C$_1$-C$_{18}$-alkyl)$_3$SnX$_3$ or B(O—C$_1$-C$_4$-alkyl)$_3$.

2. Ferrocene, bisindenylferrocene or ruthenocene having a structural element of the formula I in the aromatic hydrocarbon ring,

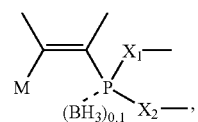 (I)

where
M, X$_1$ and X$_2$ are as defined in claim 1 and the group —C=C— together with carbon atoms forms a hydrocarbon aromatic.

3. Ferrocene, bisindenylferrocene or ruthenocene as claimed in claim 2, characterized in that they have a ferrocene skeleton and correspond to the formula Ib or Ic,

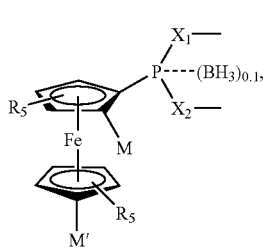 (Ib)

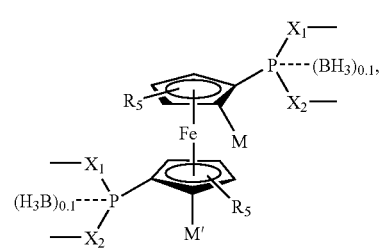 (Ic)

where
R$_5$ is C$_1$-C$_4$-alkyl and preferably a hydrogen atom,
M is —MgCl, —MgBr and preferably Li,
M' is H, —MgCl, —MgBr or Li and
X$_1$ and X$_2$ are each, independently of one another, O or N and C-bonded hydrocarbon or heterohydrocarbon radicals are bound to the free bonds of the O or N atoms.

4. A process for preparing ferrocene, bisindenylferrocene or ruthenocene having a structural element of the formula III,

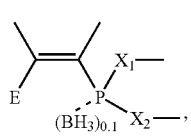 (III)

where
X$_1$ and X$_2$ and also the radicals bound to free bonds have the meanings given in claim 1 and E is the radical of a reactive, electrophilic compound which is able to replace a metal bound to hydrocarbon aromatics or a bound metal group, characterized in that ferrocene, bisindenylferrocene or ruthenocene having a structural element of the formula I,

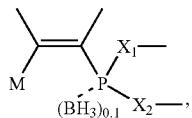

(I)

where
M, $X_1$ and $X_2$ and the radicals bound to free bonds have the meanings given in claim 1, is reacted with at least equivalent amounts of a reactive electrophilic compound.

5. A metallocene from the group consisting of ferrocene, bisindenylferrocene and ruthenocene having a structural element of the formula III in one or both cyclopentadienyl rings,

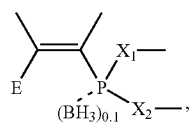

(III)

where
E is the radical of a reactive, electrophilic compound which is able to replace a metal bound to hydrocarbon aromatics or a bound metal group, $X_1$ and $X_2$ and hydrocarbon radicals bound to the free bonds of the groups $X_1$ and $X_2$ have the meanings given in claim 1.

6. The metallocene as claimed in claim 5, characterized in that it corresponds to the formula IV,

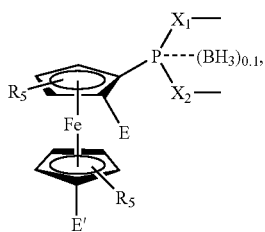

(IV)

where
$R_5$ is $C_1$-$C_4$-alkyl and preferably a hydrogen atom, E' is H or independently has one of the meanings of E, and E, $X_1$ and $X_2$ and hydrocarbon radicals bound to the free bonds of the groups $X_1$ and $X_2$ have the meanings given in claim 5.

7. The metallocene as claimed in claim 5, characterized in that it corresponds to the formula Iva,

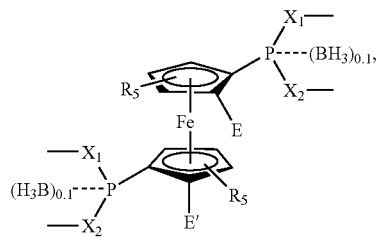

(IVa)

where
E' is H or independently has one of the meanings of E,
$R_5$ is $C_1$-$C_4$-alkyl and preferably a hydrogen atom and
E, $X_1$ and $X_2$ and hydrocarbon radicals bound to the free bonds of the groups $X_1$ and $X_2$ have the meanings given in claim 5.

8. A process for preparing ferrocene, bisindenylferrocene or ruthenocene diphosphines having structural elements of the formula VI in an aromatic hydrocarbon ring,

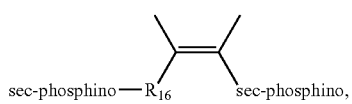

(VI)

or having structural elements of the formula VIa in each cyclopentadienyl ring of a metallocene,

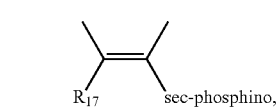

(VIa)

where
$R_{16}$ is a direct bond or a divalent bridging group, with the sec-phosphino in the bridging group being located in the 1, 2 or 3 position relative to the carbon atom of the aromatic ring, and
$R_{17}$ is a substituent which is bound via a carbon atom to the aromatic ring, which comprises the steps:
a) reaction of ferrocenes, bisindenylferrocenes or ruthenocenes having structural elements of the formula II

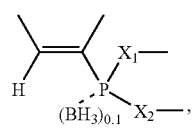

(II)

with metalation reagents to form a ferrocene, bisindenylferrocene or ruthenocene having structural elements of the formula I

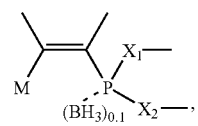

(I)

where M, $X_1$ and $X_2$ and hydrocarbon radicals bound to the free bonds of the groups $X_1$ and $X_2$ have the meanings given in claim 1, b) reaction of ferrocenes, bisindenylferrocenes or ruthenocenes having structural elements of the formula I with an electrophilic and reactive compound, wherein b1) the compound of the formula I is reacted with a sec-phosphine halide to introduce sec-phosphino, b2) the compound of the formula I is reacted with an electrophilic reactive compound which has a reactive group which can be replaced by sec-phosphino in the 1, 2 or 3 position and the product is subsequently reacted with a metal sec-phosphate or a secondary phosphine to introduce the group —$R_{16}$-sec-phosphino, b3) the compound of the formula I with an electrophilic organic compound which forms an α-carbon atom to introduce the group —$R_{17}$, c) any borane group present is removed from the compounds obtained in steps b1), b2) or B3) and the radicals (hetero)hydrocarbon-$X_1$, (hetero)hydrocarbon-$X_2$ or $X_1$-(hetero)hydrocarbon-$X_2$ are subsequently split off to form a —$PCl_2$ group or —$PBr_2$ group and the Cl or Br atoms are then replaced by a hydrocarbon radical by means of an organometallic compound to form the sec-phosphino group, or d) the radicals (hetero)hydrocarbon-$X_1$, (hetero)hydrocarbon-$X_2$ or $X_1$-(hetero)hydrocarbon-$X_2$ are split off to form a —$PCl_2$ group or —$PBr_2$ group and the Cl or Br atoms are then replaced by a hydrocarbon radical by means of an organometallic compound (Grignard reagent) to form the sec-phosphino group and the borane group is then removed.

9. A process for preparing 1-(α-substituted ortho-sec-phosphinobenzyl)-2-sec-phosphinoferrocenes of the formula VII in the form of their racemates, mixtures of diastereomers or essentially pure diastereomers,

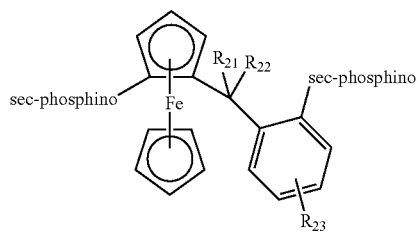

(VII)

where
$R_{21}$ is hydrogen, $C_1$-$C_6$-alkyl, $C_3$-$C_8$-cycloalkyl, unsubstituted or F—, $C_1$-$C_6$-alkyl- or $C_1$-$C_6$-alkoxy-substituted phenyl or benzyl,
$R_{22}$ is $C_1$-$C_4$-alkoxy, $C_1$-$C_8$-acyloxy or sec-amino and
$R_{23}$ is hydrogen, $C_1$-$C_4$-alkyl or $C_1$-$C_4$-alkoxy,
which comprises the steps:
a) reaction of a compound of the formula VIII

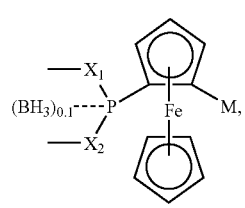

(VIII)

where
M and the group —P($X_1$—)($X_2$—) - - - $(BH_3)_{0,1}$ are as defined in claim 1, with a compound of the formula IX

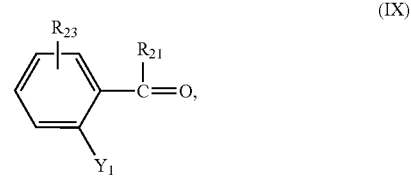

(IX)

where $Y_1$ is Cl, Br or I and $R_{23}$ and $R_{21}$ are as defined in claim 1, to form a compound of the formula X,

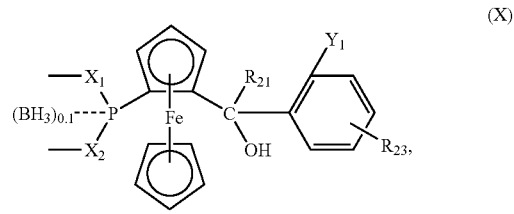

(X)

b) $C_1$-$C_4$-alkylation or $C_1$-$C_8$-acylation of the OH group in the compound of the formula X or replacement of the acyloxy group formed by sec-amino, c) replacement of the halogen $Y_1$ in compounds of the formula X by sec-phosphino and subsequent conversion of the group —P($X_1$—)($X_2$—) - - - $(BH_3)_{0,1}$ into a sec-phosphino group, or conversion of the group —P($X_1$—)($X_2$—) - - - $(BH_3)_{0,1}$ firstly into a sec-phosphino group and subsequent replacement of the halogen $Y_1$ in compounds of the formula X by sec-phosphino, d) preparation of the diphosphine of the formula VII, by d1) removing any borane group present from a compound of the formula X, then splitting off the radicals (hetero)hydrocarbon-$X_1$, (hetero)hydrocarbon-$X_2$ or $X_1$-(hetero)hydrocarbon-$X_2$ to form a —$PCl_2$ group or —$PBr_2$ group and then replacing the Cl or Br atoms by a hydrocarbon radical by means of an organometallic compound (Grignard reagent) to form the sec-phosphino group, or d2) splitting off the radicals (hetero)hydrocarbon-$X_1$, (hetero)hydrocarbon-$X_2$ or $X_1$-(hetero)hydrocarbon-$X_2$ to form a —$PCl_2$ group or —$PBr_2$ group and then replacing the Cl or Br atoms by a hydrocarbon radical by means of an organometallic compound (Grignard reagent) to form the sec-phosphino group and then removing the borane group.

10. A compound of the formula XI in the form of a racemate, diastereomer or pair of diastereomers,

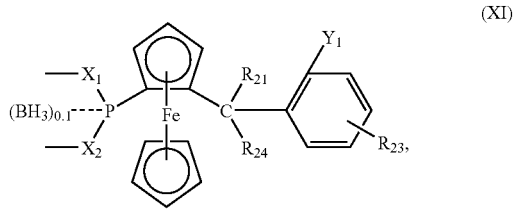

(XI)

where
X$_1$ and X$_2$ are each, independently of one another, O or N and C-bonded hydrocarbon or heterohydrocarbon radicals are bound to the free bonds of the O or N atoms, R$_{21}$, R$_{23}$ and Y$_1$ are as defined in claim 9, or (X$_1$—) and (X$_2$—) in the group —P(X$_1$—)(X$_2$—) - - - (BH$_3$)$_{0.1}$ are Cl or Br, and R$_{24}$ is —OH, C$_1$-C$_4$-alkoxy, C$_1$-C$_8$-acyloxy or sec-amino.

11. A process for preparing compounds of the formula XII in the form of racemates, diastereomers and pairs of diastereomers,

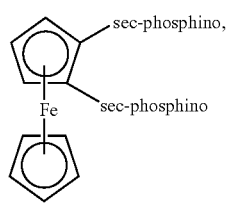

(XII)

which comprises the steps
a) reaction of a compound of the formula XIV

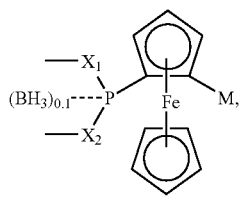

(XIV)

where
M, and the group —P(X$_1$—)(X$_2$—) - - - (BH$_3$)$_{0.1}$ are as defined in claim 1, with a sec-phosphine halide (chloride or bromide) to produce compounds of the formula XVI,

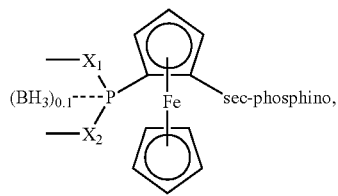

(XVI)

b) preparation of diphosphines of the formulae XII by
b1) removing any borane group present from a compound of the formula XVI or XVII, then splitting off the radicals (hetero)hydrocarbon-X$_1$, (hetero)hydrocarbon-X$_2$ or X$_1$-(hetero)hydrocarbon-X$_2$ to form a —PCl$_2$ group or —PBr$_2$ group and then replacing the Cl or Br atoms by a hydrocarbon radical by means of an organometallic compound (Grignard reagent) to form the sec-phosphino group, or
b2) splitting off the radicals (hetero)hydrocarbon-X$_1$, (hetero)hydrocarbon-X$_2$ or X$_1$-(hetero)hydrocarbon-X$_2$ to form a —PCl$_2$ group or —PBr$_2$ group and then replacing the Cl or Br atoms by a hydrocarbon radical by means of an organometallic compound (Grignard reagent) to form the sec-phosphino group and then removing the borane group.

12. The process as claimed in claim 8 for preparing compounds of the formula XXIV in the form of racemates, diastereomers and pairs of diastereomers,

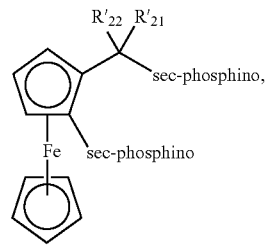

(XXIV)

where
R'$_{21}$ is hydrogen or C$_1$-C$_6$-alkyl,
R'$_{22}$ is C$_1$-C$_6$-alkyl, C$_3$-C$_8$-cycloalkyl, unsubstituted or F—, C$_1$-C$_6$-alkyl- or C$_1$-C$_6$-alkoxy-substituted phenyl or benzyl, which comprises the steps
a) reaction of a compound of the formula XX,

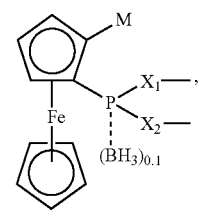

(XX)

with an aldehyde or ketone of the formula R'$_{21}$R'$_{22}$C(O) to form a compound of the formula XXV,

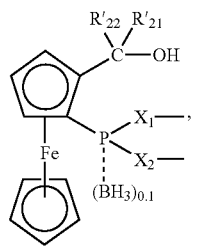

(XXV)

b) preparation of compounds of the formula XXVI,

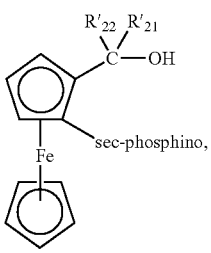

(XXVI)

by
b1) removing any borane group present from a compound of the formula XXV, then splitting off the radicals (hetero)hydrocarbon-$X_1$, (hetero)hydrocarbon-$X_2$ or $X_1$-(hetero)-hydrocarbon-$X_2$ to form a —$PCl_2$ group or —$PBr_2$ group and then replacing the Cl or Br atoms by a hydrocarbon radical by means of an organometallic compound (Grignard reagent) to form the sec-phosphino group, or b2) splitting off the radicals (hetero)hydrocarbon-$X_1$, (hetero)hydrocarbon-$X_2$ or $X_1$-(hetero)hydrocarbon-$X_2$ to form a —$PCl_2$ group or —$PBr_2$ group and then replacing the Cl or Br atoms by a hydrocarbon radical by means of an organometallic compound (Grignard reagent) to form the sec-phosphino group and then removing the borane group, c) acylating the compound of the formula XXVI, for example by means of a carboxylic anhydride, and d) replacing the $C_1$-$C_8$-acyloxy group formed by means of a secondary phosphine to give compounds of the formula XXIV.

13. The process as claimed in claim 8 for preparing compounds of the formula XXIX in the form of racemates, diastereomers and pairs of diastereomers,

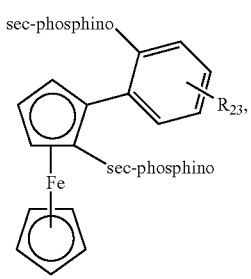

(XXIX)

which comprises the steps a) reaction of a compound of the formula XX

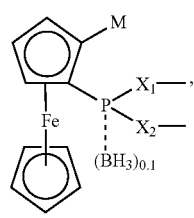

(XX)

where M is —Sn($C_1$-$C_4$-alkyl)$_3$ or —$ZnX_3$, $X_1$ and $X_2$ are each, independently of one another, O or N and C-bonded hydrocarbon or heterohydrocarbon radicals are bound to the free bonds of the O or N atoms, with 1-bromo-2-iodobenzene or 1,2-diiodobenzene in the presence of a Pd catalyst to form a compound of the formula XXX,

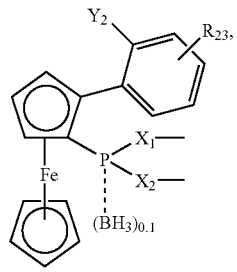

(XXX)

where $Y_2$ is bromine or iodine, b) to prepare monophosphines of the formula XXXI

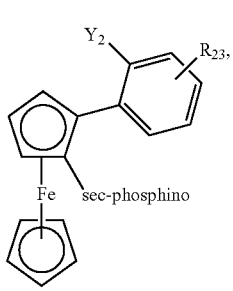

(XXXI)

b1) removing any borane group present from a compound of the formula XXX, then splitting off the radicals (hetero)hydrocarbon-$X_1$, (hetero)hydrocarbon-$X_2$ or $X_1$-(hetero)-hydrocarbon-$X_2$ to form a —$PCl_2$ group or —$PBr_2$ group and then replacing the Cl or Br atoms by a hydrocarbon radical by means of an organometallic compound (Grignard reagent) to form the sec-phosphino group, or b2) splitting off the radicals (hetero)hydrocarbon-$X_1$, (hetero)hydrocarbon-$X_2$ or $X_1$-(hetero)hydrocarbon-$X_2$ to form a —$PCl_2$ group or —$PBr_2$ group and then replacing the Cl or Br atoms by a hydrocarbon radical by means of an organometallic compound (Grignard reagent) to form the sec-phosphino group and then removing the borane group, and c) then replacing the bromine or iodine atom by a sec-phosphino group by metalation by means of a lithium alkyl (butyllithium) and subsequent reaction with a sec-phosphine halide, or d) to prepare compounds of the formula XXXII

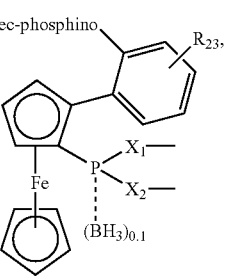

(XXXII)

reacting a compound of the formula XX with ortho-sec-phosphinophenyl iodide in the presence of metal halides such as $ZnBr_2$ and Pd catalysts, and d1) removing any borane group present from a compound of the formula XXXII, then splitting off the radicals (hetero)hydrocarbon-$X_1$, (hetero)hydrocarbon-$X_2$ or $X_1$-(hetero)-hydrocarbon-$X_2$ to form a —$PCl_2$ group or —$PBr_2$ group and then replacing the Cl or Br atoms by a hydrocarbon radical by means of an organometallic compound (Grignard reagent) to form the sec-phosphino group, or d2) splitting off the radicals (hetero)hydrocarbon-$X_1$, (hetero)hydrocarbon-$X_2$ or $X_1$-(hetero)hydrocarbon-$X_2$ to form a —$PCl_2$ group or —$PBr_2$ group and then replacing the Cl or Br atoms by a hydrocarbon radical by means of an organometallic compound (Grignard reagent) to form the sec-phosphino group and then removing the borane group.

14. The process as claimed in claim 8 for preparing compounds of the formula XXXV in the form of racemates, diastereomers and pairs of diastereomers,

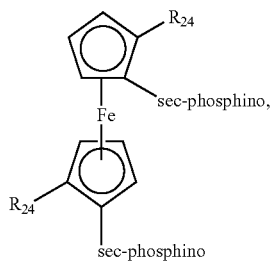

(XXXV)

where
$R_{24}$ is a radical of the formula —$CR_{25}R_{26}$—$Y_3$ or a group $R_{28}$,
$R_{25}$ is hydrogen, $C_1$-$C_6$-alkyl, $C_3$-$C_8$-cycloalkyl, unsubstituted or F—, $C_1$-$C_6$-alkyl- or $C_1$-$C_6$-alkoxy-substituted phenyl or benzyl,
$R_{26}$ is $C_1$-$C_6$-alkyl, $C_3$-$C_8$-cycloalkyl, unsubstituted or F—, $C_1$-$C_6$-alkyl- or $C_1$-$C_6$-alkoxy-substituted phenyl or benzyl,
$Y_3$ is $C_1$-$C_4$-alkoxy, $C_1$-$C_8$-acyloxy or sec-amino and
$R_{28}$ is $C_1$-$C_6$-alkyl, $C_3$-$C_8$-cycloalkyl, unsubstituted or F—, $C_1$-$C_6$-alkyl- or $C_1$-$C_6$-alkoxy-substituted phenyl or benzyl,
which comprises the steps
a) reaction of a compound of the formula XXXVI

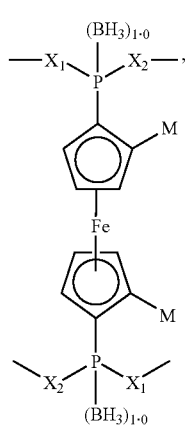

(XXXVI)

where
$X_1$ and $X_2$ are each, independently of one another, O or N and C-bonded hydrocarbon or heterohydrocarbon radicals are bound to the free bonds of the O or N atoms, with an aldehyde or ketone or imine of the formula $CR_{25}R_{26}$=$Y_4$, where $Y_4$ is =O or =$N(C_1$-$C_4$-alkyl), or with a halide $R_{28}Y_6$, where $Y_6$ is Cl, Br or iodine, to form compounds of the formula XXXVII

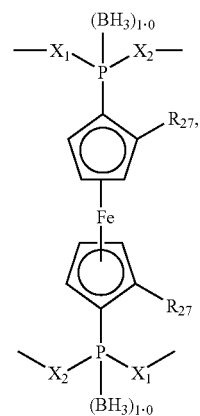

(XXXVII)

where
$R_{27}$ is the group —$CR_{25}R_{26}$—$Y_5$ or $R_{28}$, where $R_{25}$ and $R_{26}$ are as defined above and $Y_5$ is —OH or —$NH(C_1$-$C_4$-alkyl), alkylating the NH group, if appropriate alkylating or acylating the OH group and, if appropriate, replacing the acyloxy group by sec-amino and b) to prepare compounds of the formula XXXV b1) removing any borane group present from a compound of the formula XXXVII, then splitting off the radicals (hetero)hydrocarbon-$X_1$, (hetero)hydrocarbon-$X_2$ or $X_1$-(hetero)-hydrocarbon-$X_2$ to form a —$PCl_2$ group or —$PBr_2$ group and then replacing the Cl or Br atoms by a hydrocarbon radical by means of an organometallic compound (Grignard reagent) to form the sec-phosphino group, or b2) splitting off the radicals (hetero)hydrocarbon-$X_1$, (hetero)hydrocarbon-$X_2$ or $X_1$-(hetero)hydrocarbon-$X_2$ to form a —$PCl_2$ group or —$PBr_2$ group and then replacing the Cl or Br atoms by a hydrocarbon radical by means of an organometallic compound (Grignard reagent) to form the sec-phosphino group and then removing the borane group.

* * * * *